(12) United States Patent
Serhan et al.

(10) Patent No.: US 7,341,840 B2
(45) Date of Patent: Mar. 11, 2008

(54) METHODS FOR IDENTIFICATION AND USES OF ANTI-INFLAMMATORY RECEPTORS FOR EICOSAPENTAENOIC ACID ANALOGS

(75) Inventors: Charles N. Serhan, Needham, MA (US); Makoto Arita, Brookline, MA (US)

(73) Assignee: The Brigham and Women's Hospital, Inc., Boston, MA (US)

(*) Notice: Subject to any disclaimer, the term of this patent is extended or adjusted under 35 U.S.C. 154(b) by 161 days.

(21) Appl. No.: 11/218,281

(22) Filed: Sep. 1, 2005

(65) Prior Publication Data

US 2006/0024758 A1    Feb. 2, 2006

Related U.S. Application Data

(63) Continuation of application No. PCT/US2004/006766, filed on Mar. 5, 2004.

(60) Provisional application No. 60/452,244, filed on Mar. 5, 2003.

(51) Int. Cl.
  G01N 33/53    (2006.01)
  G01N 33/567   (2006.01)
(52) U.S. Cl. .................. 435/7.2; 435/7.24
(58) Field of Classification Search .......... None
  See application file for complete search history.

(56) References Cited

U.S. PATENT DOCUMENTS

| | | |
|---|---|---|
| 4,201,211 A | 5/1980 | Chandrasekaran et al. |
| 4,442,099 A | 4/1984 | Nicolaou et al. |
| 4,567,290 A | 1/1986 | Nicolaou et al. |
| 4,576,758 A | 3/1986 | Morris et al. |
| 4,666,701 A | 5/1987 | Horrobin et al. |
| 4,710,521 A | 12/1987 | Soukup et al. |

(Continued)

FOREIGN PATENT DOCUMENTS

EP    0736509 A2    10/1996

(Continued)

OTHER PUBLICATIONS

XP 002184773.

(Continued)

*Primary Examiner*—Prema Mertz
(74) *Attorney, Agent, or Firm*—Scott D. Rothenberger; Dorsey & Whitney LLP

(57) ABSTRACT

The present invention is directed to methods for the identification and uses of receptors that interact with anti-inflammatory compounds derived from eicosapentaenoic acid (EPA). The receptors are of the G-protein coupled receptor (GPCR) family, and are useful to screen candidate substances for anti-inflammatory activity, especially substances that are analogs of EPA. Such analogs are termed "resolvins"; and are typically di- and tri-hydroxy EPA analogs. One analog herein denoted Resolvin E1 was identified in humans and prepared by total synthesis. In nanomolar range Resolvin E1 reduces dermal inflammation, peritonitis, dendritic cells (DCs) migration and IL-12 production. Also described herein is a receptor denoted Reso ER1 that interacts with Resolvin E1 to attenuate cytokine induced activation of inflammatory pathways mediated by transcription factor (NF)-kB. Treatment of DCs with small-interfering RNA specific for ResoE1 eliminated the ligand's ability to regulate IL-12. Assays of anti-inflammatory activity based on these discoveries are also described.

8 Claims, 7 Drawing Sheets

U.S. PATENT DOCUMENTS

| | | | |
|---|---|---|---|
| 4,759,880 | A | 7/1988 | Nicolaou et al. |
| 4,810,424 | A | 3/1989 | Gerwick et al. |
| 5,087,790 | A | 2/1992 | Petasis et al. |
| 5,136,501 | A | 8/1992 | Silverman et al. |
| 5,177,046 | A | 1/1993 | Savoca et al. |
| 5,409,955 | A | 4/1995 | Bockow et al. |
| 5,411,988 | A | 5/1995 | Bockow et al. |
| 5,441,951 | A | 8/1995 | Serhan |
| 5,594,732 | A | 1/1997 | Bell et al. |
| 5,604,258 | A | 2/1997 | Ferrante et al. |
| 5,648,512 | A | 7/1997 | Serhan |
| 5,709,855 | A | 1/1998 | Bockow |
| 5,752,238 | A | 5/1998 | Dedrick |
| 5,756,789 | A | 5/1998 | Bruce et al. |
| 5,814,599 | A | 9/1998 | Mitragotri et al. |
| 5,842,040 | A | 11/1998 | Hughes et al. |
| 5,845,265 | A | 12/1998 | Woolston |
| 5,846,974 | A | 12/1998 | Kallman et al. |
| 5,870,717 | A | 2/1999 | Wiecha |
| 5,878,400 | A | 3/1999 | Carter, III |
| 5,878,423 | A | 3/1999 | Anderson et al. |
| 5,890,138 | A | 3/1999 | Godin et al. |
| 5,896,379 | A | 4/1999 | Haber |
| 5,932,598 | A | 8/1999 | Talley et al. |
| 5,946,467 | A | 8/1999 | Pathakis et al. |
| 6,030,715 | A | 2/2000 | Thompson et al. |
| 6,030,917 | A | 2/2000 | Weinberg et al. |
| 6,048,897 | A | 4/2000 | Serhan |
| 6,069,109 | A | 5/2000 | Kao et al. |
| 6,117,911 | A | 9/2000 | Grainger et al. |
| 6,201,022 | B1 | 3/2001 | Mease et al. |
| 6,232,467 | B1 | 5/2001 | Petasis et al. |
| 6,259,699 | B1 | 7/2001 | Opalka et al. |
| 6,272,474 | B1 | 8/2001 | Garcia |
| 6,316,648 | B1 | 11/2001 | Serhan |
| 6,336,138 | B1 | 1/2002 | Caswell et al. |
| 6,377,937 | B1 | 4/2002 | Paskowitz |
| 6,397,212 | B1 | 5/2002 | Biffar |
| 6,415,270 | B1 | 7/2002 | Rackson et al. |
| 6,427,132 | B1 | 7/2002 | Bowman-Amuah |
| 6,428,900 | B1 | 8/2002 | Pradip et al. |
| 6,569,075 | B2 | 5/2003 | Serhan |
| 6,602,817 | B1 | 8/2003 | Petasis |
| 6,620,919 | B2 | 9/2003 | Serhan |
| 6,635,776 | B2 | 10/2003 | Serhan |
| 6,653,493 | B2 | 11/2003 | Serhan |
| 6,670,396 | B2 | 12/2003 | Serhan et al. |
| 6,750,360 | B2 | 6/2004 | Serhan |
| 6,887,901 | B1 | 5/2005 | Serhan |
| 2001/0023500 | A1 | 9/2001 | Serhan |
| 2002/0010351 | A1 | 1/2002 | Serhan |
| 2002/0031882 | A1 | 3/2002 | Serhan |
| 2002/0045579 | A1 | 4/2002 | Madara et al. |
| 2002/0055538 | A1 | 5/2002 | Serhan et al. |
| 2002/0082435 | A1 | 6/2002 | Serhan |
| 2002/0091279 | A1 | 7/2002 | Serhan |
| 2002/0094549 | A1 | 7/2002 | Serhan et al. |
| 2002/0107289 | A1 | 8/2002 | Serhan |
| 2002/0120013 | A1 | 8/2002 | Serhan |
| 2002/0132847 | A1 | 9/2002 | Serhan |
| 2002/0143069 | A1 | 10/2002 | Serhan |
| 2002/0193431 | A1 | 12/2002 | Serhan et al. |
| 2003/0032827 | A1 | 2/2003 | Serhan |
| 2003/0055275 | A1 | 3/2003 | Serhan |
| 2003/0060512 | A1 | 3/2003 | Madara et al. |
| 2003/0069435 | A1 | 4/2003 | Serhan |
| 2003/0134901 | A1 | 7/2003 | Serhan |
| 2003/0166716 | A1 | 9/2003 | Serhan et al. |
| 2003/0191184 | A1 | 10/2003 | Serhan et al. |
| 2003/0191332 | A1 | 10/2003 | Serhan |
| 2003/0195248 | A1 | 10/2003 | Serhan et al. |
| 2003/0236423 | A1 | 12/2003 | Petasis |
| 2004/0019110 | A1 | 1/2004 | Van Dyke et al. |
| 2004/0053998 | A1 | 3/2004 | Serhan et al. |
| 2004/0059144 | A1 | 3/2004 | Serhan et al. |
| 2004/0116408 | A1 | 6/2004 | Serhan |
| 2004/0151712 | A1 | 8/2004 | Madara et al. |
| 2004/0192785 | A1 | 9/2004 | Serhan |
| 2005/0075398 | A1 | 4/2005 | Bazan et al. |
| 2005/0261255 | A1 | 11/2005 | Serhan et al. |

FOREIGN PATENT DOCUMENTS

| | | |
|---|---|---|
| EP | 0736509 B1 | 11/2001 |
| JP | 5186342 | 7/1993 |
| WO | WO 91/16914 | 11/1991 |
| WO | WO 97/19415 | 5/1997 |
| WO | WO 98/19259 | 5/1998 |
| WO | WO 98/35469 | 8/1998 |
| WO | WO 98/46588 | 10/1998 |
| WO | WO 99/06913 | 2/1999 |
| WO | WO 99/13417 | 3/1999 |
| WO | WO 01/60778 | 8/2001 |
| WO | WO 03/051350 | 6/2003 |
| WO | WO 03/053423 | 7/2003 |
| WO | WO 03/084305 A | 10/2003 |
| WO | WO 03/105776 A | 12/2003 |
| WO | WO 2004/014835 | 2/2004 |
| WO | WO 2005/089744 A | 9/2005 |

OTHER PUBLICATIONS

Arita, et al., "Resolvin E1, An Endogenous Lipid Mediator Derived from Omega-3 Eicosapentaenoic Acid, Protects Against 2, 4,6-Trinitrobenzene Sulfonic Acid-Induced Colitis", *Proc. Natl. Acad. Sci*, USA, 102(21): 7671-7676, 2005.

Arita et al., "Stereochemical Assignment, Antiinflammatory Properties, and Receptor for the Omega-3 Lipid Mediator Resolvin E1", *J. Exp. Med.* 201(5): 713-722, 2005.

Bannenberg, et al., "Molecular Circuits of Resolution: Formation and Actions of Resolvins and Protectins", *Immunol.* 174(7): 4345-4355, 2005.

Beamer L.J. et al. "Crystal structure of Human BPI and two bound phospholipids at 2.4 angstrom resolution", *Science*, vol. 276, 1997, pp. 1861-1864.

Hong, et al., "Novel Docosatrienes and 17S-Resolvins Generated from Docosahexaenoic Acid in Murine Brain, Human Blood, and Glial Cells, Autacoids in Anti-Inflammation", *J. Biol. Chem.* 278(17): 14677-14687, 2003.

Marcheselli, et al. "Novel Docosanoids Inhibit Brain Ischemia-Reperfusion-Mediated Leukocyte Infiltration and Pro-Inflammatory Gene Expression", *J. Biol. Chem.* 278(44): 43807-43817, 2003.

Serhan, et al., "Novel Pathways and Endogenous Mediators in Anti-Inflammation and Resolution", *Chem Immunol Allergy*, 83: 115-145, 2003.

Serhan, "Novel Omega-3-Derived Local Mediators in Anti-Inflammation and Resolution", *Pharmacol. Ther.* 105(1): 7-21, 2005.

Serhan, et al., "Novel Endogenous Small Molecules as the Checkpoint Controllers in Inflammation and Resolution: Entrée for Resoleomics" *Rheum Dis Clin North Am.* 30(1): 69-95, 2004.

Serhan et al., Resolvins, Docosatrienes, and Neuroprotectins, Novel Omega-3-Derived Mediators, and Their Aspirin-Triggered Endogenous Epimers: An Overview of Their Protective Roles in Catabasis, *Prostaglandins Other Lipid Mediat.* 5543, 1-18, 2004.

Serhan, "A Search for Endogenous Mechanisms of Anti-Inflammation Uncovers Novel Chemical Mediators: Missing Links to Resolution", *Histochem Cell Biol.* 122(4): 305-321, 2004.

Serhan, "Novel Eicosanoid and Docosanoid Mediators: Resolvins, Docosatrienes, and Neuroprotectins", *Curr Opin Clin Nutr Metab Care*, 8(2): 1-7, 2005.

Van Dyke, et al., "Resolution of Inflammation: A New Paradigm for the Pathogenesis of Periodontal Diseases", *J. Dent. Res.*, 82(2): 82-90, 2003.

Serhan, et al., "Resolvins: a family of bioactive products of omega-3 fatty acids transformation circuits initiated by aspirin treatment that counter proinflammation signals", *J. Exp. Med.*, vol. 196, No. 8 pp. 1025-1037, 2002.

Serhan, et al., Resolvins, Docosatrienes and Neuroprotectins, Novel Omega-3 Derived Mediators and Their Endogenous Aspirin-Triggered Epimers, *Lipids*, vol. 39, pp. 1125-1132, 2004.

Takeshi Terano, Ensho, Chemical Abstract 107:22439, pp. 63-71, 1987.

Terano T. et al., "Eicosapentaenoic acid and docosahexaenoic acid inhibit vascular smooth muscle cell proliferation by inhibiting phosphorylation of Cdk2-cyclinE complex", *Biochem. Biophys. Res. Comm.*, vol. 254, pp. 502-506.

W.E.M. Lands, "Proceedings of the AOCS Short Course on Polyunsaturated Fatty Acids and Eicosanoids", *American Oil Chemists' Society* 1987.

Miller et al., Lipids, Chemical Abstract 112:117062, pp. 998-1003, 1989.

Hill, E.M., *Proc R. Soc. London Ser. B.*, 247 (1318) pp. 41-46, 1992.

Eritsland et al., "Effects of Highly Concentrated Omega-3 PUF As and Acetylsalicylic Acid, Alone and Combined, on Bleeding Time and Serum Liquid Profile", *J. Oslo City Hosp.*, vol. 39 (8-9), pp. 97-101, 1989.

Iacoviello et al., "Modulation of Fibrinolytic Response to Venous Occulusion in Humans by a Combination of Low-Dose Aspirin and n-3 PUFAs", *Arteriosclerosis Thrombosis*, vol. 10, pp. 1191-1197, 1992.

Lau et al., "Effects of Fish Oil Supplementation on Non-Steroidal Anti-Inflammatory Drug (NSAID) Requirement in Patients with Mild Rheumatoid Arthritis—A Double-Blind Placebo Controlled Study", *British Journal of Rheumatology*, vol. 32 (11), pp. 982-989. 1993.

Rao et al, "Comparative Pharmacology of Cyclooxygenase Inhibitors on Platelet Function", *Prostaglandins Leukot. Med.*, vol. 18 (1), pp. 119-131, 1985.

CA 101:19194 for VanRollins et al., *Journal of Biological Chemistry*,(1984) 259(9), pp. 5776-5783.

CA 119: 265901 for Reynaud et al., *Analytical Biochemistry* (1993), 214(1), pp. 165-170.

Canny, G. et al., "Lipid mediator-induced expression of bactericidal/permeability-increasing protein (BPI) in human mucosal epithelia", *Proc. Natl. Acad., Sci., USA*, vol. 99, No. 6, 2002, pp. 3902-3907.

Dharmsathaphorn, K. et al., "Established intestinal cell lines as model systems for electrolyte transport studies", *Methods in Enzymology*, vol. 192, 1990, pp. 354-389.

Eckmann, L. et al., Epithelial cell secrete the chemokines interleukin-8 in response to bacterial entry, *Infection and Immunity*, vol. 61, No. 11, 1193, pp. 4569-4574.

Alami, et al., A versatile route to conjugated hydroxyl (E,Z,E,E)—Tetraenoic acids: highly chemo- and stereoselective synthesis of lipoxin B4 tetrahedro Asym. 8(17): 2949-2958, 1997.

Babine, R.E. and S.L. Bender., "Molecular Recognition of Protein-Ligand Complexes: Applications to Design" *Chem. Rev.* 97:1359-1472 (1997).

Bhaley, G. et al., Solid Phase Synthesis of Diverse Tetrahydro-1,4-Benzodiazepine-2-ones, *Tetrahedron Letters* 38(48):8375-8378 (1997).

Blaser, E. et al., "Asymmetrix Steering of oxa Diels-Alder Reactions with Silyloxydienes Employing Proline Esters as Chiral Auxillary Groups," *Eur. J. Org. Chem.*, 329-333, (1999).

Boland et al., "Stereospecific Syntheses and Spectroscopis Properties of Isomeric 2,4,6,8-Undecatetraenes. New Hydrocarbons from the Marine Brown Alga Giffordia Mitchellae", *Helv. Chim. Acta* 70;1025-1040, 1987.

Dioux, Laurent and Morris Srebnik, "Asymmetric Boron-Catalyzed Reactins", *Chem Rev.* 93:763-784, (1993).

Durantel et al., "Study of the mechamism of Antiviral Action of Iminosugar Derivatives against Bovine Viral Diarrhea Virus", *J. Virology* 75 (19): 8987-8998, 2001.

Vu Bois e tal., "Novel, Stereoselcetive Synthesis of 2 Amino Saccharides", *J. Am. Chem. Soc.* 119: 3179-3180, 1997.

Evans, B.E. et al., "Design of Nonpetidal ligands for a Peptide Receptor: Cholecystokinin Antagonists", *J. Med. Chem.* 30:1229-1239 (1987).

Fletcher, M.D. and M.C. Campbell, "Partially Modified Retro-Inverso Peptides: Development, Sythesis, and Conformational Behavior," *Chem. Rev.*, 98: 763-795, (1998).

Garro-Hellon et al., "Mild and selective Palladium (0)-Catalyzed Deallylation of Allylic Amines, Allylamine and Diallylamines as Very Convenient Ammonia Equivalents for the Synthesis of Primary Amines", *J. Org. Chem.* 58: 6109-6113, (1993).

Golebiowski, A. and J. Jurczak, "Alpha-Amino-Beta-Hydroxy Acids in the Total Synthesis of Amino Sugars", *Synlett*, pp. 241-245, (Apr. 1993).

Gullier et al., "Linkers and Cleavage Stategies in Solid Phase Organic Synthesis and Combinatorial Chemistry", *Chem. Rev.*, 100:2091-2157, (2000).

Hanessia, S. et al., "Design and Synthesis of Conformationally Constraines Amino Acids as Versatile Scaffolds and Peptide Manners", *Tetrahedron Lett.*, 53:12789-12854, (1997).

Hoyng, C.F. and A.D. Patel, "Aldehyde Components for use in Four-Component Condensation ("4CC") UGI Reaction Peptide Synthesis," *Tetrahedron Lett.*, 21:4795-4798, (1980).

Humphrey, J.M. and A.R. Chamberlin, "Chemical Synthesis of Natural Product Peptides Coupling Methods for the Incorporation of noncoded Amino Acids into Peptides," *Chem. Rev.*, 97;2243-2266, 91997).

Ikeda et al., "Chiral Allenylboronic Esters as Practical Reagent for Enantioselective Carbon-Carbon Bond formation Facile Synthesis of (-) Ipsenol", *J. Am. Chem, Soc.*, 108;483-4486, 1986.

Konig et al., "Synthesis of N-Tert-Alkylglyxolic Acid Amides", *Syntheses*, pp. 1233-1234, (1993), [ In German, English language abstract of 1 st page of article].

Karanian, J.W., et al., "Physiological functions of hydroxyl-docosahexaenoic acid", Abstract, XP-002200246, 1993.

E.M. Hill, et al. "Identification and egg hatching activity of monohydroxy fatty acid eicosanoids in the barnacle *Balanus balanoides*", Abstract, XP-002200247, 1992.

L. De. Montarby, et al. "Synthesis stereoselectives de metabolites hydroxyles d'acides gras polinsatures", Bulletin De La Societe Chimique de France, No. 3, pp. 419-432, 1989.

M. Yamane, et al., "Docosahexaenoic/arachidonic acid ω-hydroxylation system and differentiation in the human clonic adenocarcinoma cell line, Caco-2", *Cancer Letters*, vol. 122, pp. 51-59, 1998.

T. Kato, et al., "Production of Hydroxy Unsaturated Fatty Acids Using Crude Lipoxygenase Obtained from Infected Rice Plants", *Bull. Chem. Soc. Jpn.*, vol. 69, pp. 1663-1666, 1996.

M. Ligo et al., "Inhibitory effects of docosahexaenoic acid on colon carcinoma 26 metastasis to the lung", *Br. J. Cancer*, pp. 650-655, 1997.

G.E. Billman et al., "Prevention of sudden cardiac death by dietary pure ω-3 polyunsaturated fatty acids in dogs", *Circulation 99*, 99, pp. 2452-2457.

A.P. Simopoulos, "Workshop on the essentiality of an recommended dietary intakes for omega-6 and omega-3 fatty acids", *J. Am. Coll. Nutr.* 1999, pp. 487-489.

R. Marchioloi, "Dietary supplementation with n-3 polyunsaturated fatty acids and vitamin E after myocardial infarction: results of the GISSI-Prevenzione trial", *Lancet* 1999, pp. 447-455.

G. Weissmann, "Aspirin", *Sci. Am.* 1991, pp. 84-90.

A.J. Marcus, "Platelets: their role in hemostasis, thrombosis, and inflammation", *Inflammation: Basic Principles and Clinical Correlates* 1999, pp. 77-95.

J. Claria et al., "Aspirin triggers previously undescribed bioactive eicosanoids by human endothelial cell-leukocyte interactions", *Proc. Natl. Acad. Sci.*, USA, 1995, pp. 9475-9479.

C.N. Serhan et al, "Design of lipoxin A4 stable analogs that block transmigration and adhesion of human neutrophils", *Biochemistry*, 1995, pp. 14609-14615.

C.N. Serhan, et al., "Resolvins: A family of bioactive products of omega-3 fatty acids transformation circuits initiated by aspirin treatment that counter proinflammation signals", *J. Exp. Med.*, vol. 196, No. 8, pp. 1025-1037, 2002.

C.N. Serhan et al., "Novel functional sets of lipid-derived mediators with Anti-Inflammatory Actions generated from omega-3 fatty acids via cyclooxygenase 2-nonsteroidal anti-Inflammatory drugs and transcellular processing", *J. Exp. Med.*, vol. 192, No. 8, 2000, pp. 1197-1204.

N. Chiang et al., "Leukotriene B4 receptor transgenic mice reveal novel protective roles for lipoxins and aspirin-triggered lipoxins in reperfusion", *J. Clin. Invest.*, 1999, pp. 309-316.

H.R. Herschman, "Recent progress in the cellular and molecular biology of prostaglandin synthesis", *Trends Cardiovasc. Med.*, 1998, pp. 145-150.

P. Needleman et al., "The discovery and function of COX-2", *J. Rheumatol*, 1997, pp. 6-8.

N. Chiang et al., "Aspirin-triggered 15-epl-lipoxin A4 (ATL) generation by human leukocytes and murine peritonitis exudates: Development of a specific 15-epi-LXA4 ELISA", *J. Pharmacol. Exp. Ther.*, 1998, pp. 779-790.

G. Xiao et al., "Analysis of hydroperoxide-induced tyrosyl radicals and lipoxygenase activity in aspirin-treated human prostaglandin H synthase-2", *Biochemistry* 1997, pp. 1836-1845.

K. Node et al., "Anti-inflammatory properties of cytochrome P450 epoxygenase-derived eicosanoids", *Science* 1999, pp. 1276-1279.

S. Sethi et al., "Inhibition of phagocyte-endothelium interactions by oxidized fatty acids: A natural anti-inflammatory mechanism?", *J. Lab. Clin. Med.* 1996, pp. 27-38.

G.N. Levy, "Prostaglandin H synthases, nonsteriodal anti-inflammatory drugs, and colon cancer", *FASEB J.* 1997, pp. 234-247.

K. Gronert, et al., "Transcellular regulation of eicosanoid biosynthesis", *Eicosanoid Protocols* 1999, pp. 119-144.

H.J. George et al., "Expression purification and characterization of recombinant human Inductible prostaglandin G/H synthase from baculovirus-infected insect cells", *Protein Expres. Purif.* 1996, pp. 19-26.

J.H. Capdevila et al., "The highly stereoselective oxidation of polyunsaturated fatty acids by cytochrome P450BM-3", *J. Biol. Chem.* 1996, pp. 22663-22671.

R.T. Ruettinger et al., "Epoxidation of unsaturated fatty acids by a soluble cytochrome P-45-dependent system from *Bacillus megaterium*", *J. Biol. Chem.* 1981, pp. 5728-5734.

T.H. Lee et al., "Characterization and biologic properties of 5,12-dihydroxy derivatives of eicosapentaenoic acid, including leukotriene B5 and the double lipoxygenase product", *J. Biol. Chem.* 1984, pp. 2383-2389.

C.N. Serhan et al., "Nomenclature of lipoxins and related compounds dervived from arachidonic acid and eicosapentaenoic acid", *Prostaglandins*, 1987, pp. 201-204.

D.J. Hill et al., "Trout thrombocytes contain 12-but not 5-lipoxygenase activity", *Biochem. Biophys. Acta* 1999, pp. 63-70.

B.N. Cronstein et al., "A mechanism for the anti-inflammatory effects of corticosteriods: The glucocorticoid receptor regulates leukocyte adhesion to endothelial cells and expression of endothelial-leukocyte adhesion molecule 1 and intercellular adhesion molecule 1", *Proc. Natl. Acad. Sci.* 1992, pp. 9991-9995.

T. Yokomizo et al., "A G-protein-coupled receptor for leukotriene B4 that mediates chemotaxis", *Nature*, 1997, pp. 620-624.

M.R. Buchanan et al., "Regulation of endothelial cell and platelet receptor-ligand binding by the 12- and 15-lipoxygenase monohydroxides, 12-, 15-HETE and 13-HODE", *Prostaglandins Leukot. Essent. Fatty Acids* 1998, pp. 339-346.

P.M. Ridker et al., "Inflammation, aspirin, and the risk of cardiovascular disease in apparently healthy men", *N. Engl. J. Med.* 1997, pp. 973-979.

Knapp, Howard R., et al., "Bactericidal Effects of Polyunsaturated Fatty Acids", *The Journal of Infectious Diseases*, vol. 154, No. 1, 1986 pp. 84-94.

Cooper, S.F., et al., "Identification of Antibacterial Fatty Acids from *Phaeodactylum tricomtum* grown in dialysis culture", *The Faculty Press*, 1985, pp. 28-36.

Ganz T. et al., "Antimicrobial peptides of phagocytes and epithelia", *Seminars in Hematology*, vol. 34, No. 4, 1997, pp. 343-354.

Elsbach, P .et al., "Role of the bactericidal/permeability-increasing protein in host defence", *Current Opinion in Immunology*, vol. 10, No. 1, 1998, pp. 45-49.

Levy, O., "A neutrophil-derived anti-infective molecule: bactericidal/permeability-increasing protein", *Antimicrobial Agents and Chemotherapy*, vol. 44, No. 11, 2000, pp. 2925-2931.

Levy, O., "Antimicrobial proteins and peptides of blood: templates for novel antimicrobial agents", *Blood*, vol. 96, No. 8, 2000, pp. 2664-2672.

Lockhart, D.J. et al., "Expression monitoring by hybridixation to high-density oligonucleotide arrays", *Nature Biotechnology*, vol. 14, No. 13, 1996, pp. 1675-1680.

Higuchi, R. et al., "Kinetic PCR analysis: real time monitoring of DNA amplification reactions", "*Biotechnology*", vol. 11, 1993, pp. 1026-1030.

Taylor, C.T. et al., "Critical role of cAMP response element binding protein expression in hypoxia-elicited induction of epithelial tumor necrosis factor-a", *J. Biol. Chem.*, vol. 274, No. 27, 1999, pp. 19447-19454.

Pfaffi, M.W., "A new mathematical model for relative quantification in real-time RT-PCR", *Nucleic Acids Research*, vol. 29, No. 9, 2001, pp. 2002-2007.

Colgan, S.P .et al., "Defective in vitro motility of polymorphonuclear leuocytes of homozygote and heterozygote Chediak-Higashi cats", *Vet. Immunol. Immunopathology*, 1992, pp. 205-227.

Weersink, A., et al., "Human granulocytes express a 550-kDa lipopolysaccharide-binding protein on the cell surface that is identical to the bactericidal/permeability-increasing protein", *J. Immunology*, vol. 150, No. 1, 1993, pp. 253-263.

Weiss, J. et al., "Purification and characterization of a potent bactericidal and membrane active protein from the granules of human polymorphonuclear leukocytes", *J. Biol. Chem.*, vol. 253, No. 8, 1987, pp. 2664-2672.

Marx et al., "Synthetic Design for Combinatorial Chemistry. Solution and Polymer-Supported Synthesis of Polycyclic Lactams by Intramolecular Cyclization of Azomethane Ylides," *J. Chem. Soc.*, 119:6153-6167, (1997).

Mehta et al., "Structure—Activity Relationship of a New Class of Anti-Hepatitis B Virus Agents", *Antimicrobial Agents and Chemotherapy*, 46(12):4004-4008 (2002).

Nicolaou et al., "Novel IBX-Mediated Process for the Synthesis of Amino Sugars and Libraries Thereof", *Angew. Chem. Int. Ed. Engl.*, 39:2525-2529, (2000).

Nicolaou et al., "Lipoxins and Related Eicosanoids: Biosynthesis, Biological Properties and Chemical Synthesis," *Angew. Chem. Ed. Engl.* 30: 1100-1116, (1991).

Noyori, R. (Ed), "Enantioselective Addition of Organometallic Reagents to Carbonyl Compounds: Chirality Transfer, Multiplication and Amplification," Chapter 5 in Asymmetriccal Catalysts in Organic Synthesis, New York; Wiley & Sons, Inc. pp. 225-297 (1994).

Nugent, William A., "Chiral Lewis Acid Catalysts. Enantioselective Addition of Azide to Meso Epoxides", *J. Am. Chem. Soc.*, 114(7); 2768-2769 (1992).

O'Donnell, Martin J. and J. Falmagne, "The Synthesis of Amino Acids via Organoboranes." *J. Chem. Soc. Chem. Commun.*, No. 17, pp. 1168-1169, (Sep. 1, 1985).

Petasis, N.A. and I.A. Zavialov, "The Boronic Acid Mannich Reaction: A New Method for the Synthesis of Geometrically Pure Allylamines." *Tetrahedron Letters*, 34(4): 538-586, (1993).

Rodriguez and Spur, "Total Synthesis of aspirin-triggered 15-epl-lipoxin A4", *Tetrahedron Letters*, 42: 6057-6060, 2001.

Petasis, N.A. and I.A. Zavialov, "A New and Practical Syntrhesis of Alpha Amino Acids from Alkenyl Boronic Acids," *J. Am. Chem. Soc.*, 119(2): 445-446, (1997).

"Scope and Editorial Policy", *Organometallics*, published by the American Chemical Society 21 (1): 13A, 14A (2002).

Thompson, L.A. and J.A. Ellman, "Synthesis and Applications of Small Molecule Libraries", *Chem. Rev.*, 96:555-6000 (1996).

Waki, M. and J. Meienhofer, "Peptide Synthesis Using the Four-Component Condensation (Ugl Reaction)," *J. Am. Chem. Soc.*, 99:6075-6082, (1977).

Yamamoto, Y. and N. Asao, "Selective Reactions Using Allylic Metals", *Chem Rev.*, 93;2207-2293, (1993).

McCormick, B.A. et al., "*Salmonella typhimurium* attachment to human intestinal epithelial monolayers: transcellular signaling to subepithlial neurophils", *J. Cell Biology*, vol. 123, No. 4, 1993, pp. 895-907.

Loeschke D. et al., *Dig. Dis. Sci.*, vol. 41, 2087-94, (1996).

N.G. Bazan, et al., Docosahexaneoic Acid (22:6, n-3) is metabolized to lipoxygenase reaction products in the retina, *Biochem. Biophys. Res. Comm.*, vol. 125, pp. 741-747, 1984.

J. Booyens et al., "Some effects of the essential fatty acids linoleic acid and alpha-linolenic acid and of their metabolites gamma-linolenic acid, arachidonic acid, eicosapentaenoic acid docosahexaenoic acid, and of prostoglandins A1 AND e1 on the proliferation of human osteogenic sarcoma cells in culture", *Prostoglandins Leukot. Med.*, vol. 15, pp. 15-33, 1984.

J. Catella-Lawson et al., "Cycloxygenase Inhibitors and the antiplatelet effects of aspirin", *N. Engl. J. Med.*, vol. 345, pp. 1809-1817, 2001.

L.J. Crofford. "Rational use of analgesic and anti-inflammatory drugs", *N. Engl. J. Med.*, vol. 345, pp. 1844-1846, 2001.

C.M. Fored et al., "Acetaminohen, aspirin, anad chronic renal failure", *N. Engl. J. Med*.

B.J. Greeling et al., "Fat Intake and fatty acid profile in plasma phospholipids and adipose tissue in patients with Crohn's disease, compared with controls", *Am. J. Gastroenterol.*, vol. 94, pp. 410-417, 1999.

L.J. Jenski et al., "Docosahexaenoic acid-Induced alteration of Thy-1 and CD8 expression on murine splenocytes", *Biochem. Biophys., Acta*. 1236, pp. 39-50, 1995.

T. Khair-El-Din et al., "Transcription of the murine INOS gene is inhibited by docosahexanaenoic acid, a major constituent of fetal serum and fish oils diets inhibits IFN alpha—induced Ia—expression by murine macrophases in vitro", *J. Immuno.*, vol. 154, pp. 1296-1306, 1995.

K. Kitajka et al., "The role of n-3 ployi—unsaturated fatty acids in brain: Modulation of rat brain gene expression by dietary n-3 fatty acids", *Proc. Natl. Acad. Sci.,* USA9, pp. 2619-2624, 2002.

M. Martinez et al., Docohexaenoic acid—a new therapeutic approach to peroxisomal disorder patients: Experience with two cases, *Neurology*, vol. 43, pp. 1389-1397, 1993.

I. Marzo et al., "Biosynthesis of dochexaenoic acid in human cells, evidence that two different—desaturase activities may exist", Biochem. Biophys. Acta 1301, pp. 263-272, 1996.

C.C. Miller et al., "Oxidative metabolism of dihomogammallnolenic acid by guinea pigs epidermis: Evidence of generation of anti-inflammatory products", *Prostaglandins*, vol. 35, pp. 917-938, 1988.

R. K. Pullarkat et al., "Leukocyte docosahexaenoic acid in juvenile form of ceroidlipofuscinosis", *Neuropadiatrie*, vol. 9, pp. 127-130, 1987.

M. VanRollins et al., "Oxidation of docosahexaenoic acid by rat liver mirosomes", *J. Biol. Chem.*, vol. 259, pp. 5776-5782, 1984.

J.H. Rapp et al., "Dietary eicosapentaenoic acid and docosahexaenoic acid form fish oil", *Arteriosclerosis and Thrombosis*, vol. 11 pp. 903-911, 1991.

T.D. Reddy et al., "Change in content, incorporation and lipoxygenation of docosahexaenoic acid in retina and retinal pigment epithelium in canine ceroid lipofuscinosis", *Neuroscience Lett.* vol. 59, pp. 67-72, 1985.

K.C. Srivastava, "Docosahexaenoic acid (C22:6w3) and linoleic acid are anti-aggregatory, and alter arachodonic acid metabolism in human platelets", *Prostaglandins Leukot. Med.*, Vol.

M. VanRollins et al., Autooxidation of docosahexaenoic acid: Analysis of ten isomers of hydroxydocosahexaenoate:, *J. Lipid Res.*, vol. 25, pp. 507-517, 1984.

V.A. Ziboth et al., "Inhibition of sheep vesicular gland oxygenase by unsaturated fatty acids from skin of essential acid deficient rats", *Prostaglandins*, vol. 5, pp. 233-240, 1974.

C.N. Serhan, et al., "Novel functional sets of lipd-derived mediators with anti-inflammatory actions generated from omega-3 fatty acids via cyclooxygenase 2-nonsteroidal anti-inflammatory drugs and transcellular processing", *J. Exp. Med. Col.* 192, pp. 1197-1204, 2000.

B. Samuelson et al., "Leukotrienes and lipoxins: structures, biosynthesis, and biological effects", *Science*, vol. 237, pp. 1171-1176, 1987.

F. D. Gunstone et al., "The Lipid Handbook", 2$^{nd}$ ED., Chapmam & Hall, London, 1-551-pp. 1994.

B. Samuelson et al., "From studies of biochemical mechanisms to novel biological mediators: prostaglandin endoperoxides, thromboxanes and leukotrienes", *In Les Prix Nobel*, pp. 165-174, 1982.

D.C. Zeldin, "Epoxygenase pathways of arachidonic acid metabolism", *J. Biol. Chem.*, vol. 276, pp. 36059-36062, 2001.

R. Palmantieri, et al., "Transcellular metabolism of arachidonic acid in platelets and polymorphonuclear leukocytes activated by physiological agonists: enhancement of leukotriene B4 synthesis", *Cell-Cell Interactions in the Release of Inflammatory Mediators*, vol. 314, pp. 73-89, 1991.

C.N. Serhan et al., "Unorthodox routes to prostanoid formation: new twists in cyclooxygenase-initiated pathways" *J. Clin. Invest.*, vol. 107, pp. 1481-1489, 2001.

B.D. Levy et al., "lipid mediator class switching during acute inflammation: signals in resolution", *Nature Immunol.*, vol. 2 pp. 612-619, 2001.

B. McMahon et al., "Lipoxins: Revelations On Resolution", *Trends in Pharmacological Sciences*, vol. 22, pp. 391-395, 2001.

C. Bandeira-Mielo et al., "Cyclooxygenase-2 derived prostaglandin $E_2$ and lipoxin $A_4$ accelerate resolution of allergic edema in Antiostrongylus costaricensis-infected rats: relationship with concurrent eosinophilia", *J. Immunol.*, vol. 164, pp. 1029-1036, 2000.

A. F. Rowley et al., "Homeostasis in fish—an evolutionary perspective", *Throm. Homeost.*, vol. 77, pp. 227-233, 1997.

R. De Caterina et al., "n-e Fatty Acids and Vascular Disease", *Current Topics in Cardiovascular Disease*, Springer-Verlag, London, 1993.

J.R. Hibbein, "Fish consumption and major depression", *Lancet*, vol. 351, pp. 1213, 1998.

M. Olfson et al., "National trends in the outpatient treatment of depression", *JAMA*, vol. 287, pp. 203-209, 2002.

C.M. Albert, et al., "Blood levels of long-chain n-e fatty acids and the risk of sudden death", *N. Engl. J. Med.*, vol. 346, pp. 1113-1118, 2002.

K. Shinmura et al., "Cyclooxygenase-2 medaites the cardioprotectle effects of the late phase of ischemic preconditioning in conscious rabbits", *Proc. Natl. Acad. Sci. USA*, vol. 97, pp. 10197-10202, 2000.

GISSI-Preventive Investigators, Dietary supplementation with n-3 polyunsaturated fatty acids and vitamin E after myocardial infarction: Results of the GISSI-Prevenzione trial, *Lancet*, vol. 354, pp. 447-455, 1999.

R. Marchioli et al., Early protection against sudden death by n-3 polyunsaturated fatty acids after myocardial infarction: time-course analysis of the results of the Gruppo-Italiano per lo Studion della Sopravivenze nell'Infarto Miocardico, *Circulation*, vol. 105, pp. 1897-1903, 2002.

P. McLennan et al., "The cardiovascular protective role of the docosahexaenoic acid", *Eur. J. Pharmacol.* vol. 300, pp. 83-89, 1996.

P. Libby, "Atherosclerosis, The New View", *Sci. Am.*, vol. 286, pp. 46-55, 2002.

J.M. Drazen et al., "Heterogeneity of therapeutic responses in asthma", *Br. Med. Bull.*, vol. 56, pp. 1054-1070, 2000.

J.R. Vane et al., "Therapeutic Roles of Selective COX-2 Inhibitors", *William Harvey Press*, London, 2001.

S.W. Rolinson et al., "Spatial requirements for 15-(R)- hydroxyl-5Z,8Z,11Z,13E-eicosatetraenoic acid synthesis with the cyclooxygenase active site of murine COX-2", J. Biol. Chem., vol. 275, pp. 6586-6591, 2000.

D.W. Gilroy et al., "Inducible cyclooxygenase may have anti-inflammatory properties", *Nature Med.*, vol. 5, pp. 698-701, 1999.

N.G. Balzan et al., "Pathways for the uptake and conservation of docosahexaenoic acid in photoreceptors and synapses: biochemical and autoradiographic studies", *Can. J. Physiol. Pharmacol.*, vol. 71, pp. 690-698, 1993.

J. Whelan et al., "The unique characteristics of the purified 5-lipoxygenase from potato tubers and the proposed mechanism of formation of leukotrienes and lipoxins", *BIological Oxidation Systems*, vol. 2, pp. 765-778, 1990.

S. Fischer et al., "Uptake, release and metabolism of docosahexaenoic acid (DHA, C22:6w3) in human platelets and neutrophils", *Biochem, Biophys. RES. Commun.*, vol. 120, pp. 907-918, 1984.

T.H. Lee et al., "Effects of exogenous arachidonic, eicosapentaenoic, and docosahexaenoic acids on the generation of 5-lipoxygenase pathway products by ionophore-activated human neutrophils", *J. Clin. Invest.*, vol. 74, pp. 1922-1933, 1984.

J.A. Yergey et al., "High-performance liquid chromatography/ thermospray mass spectrometry of eicosanoids and novel oxygenated metabolites of docosahexaenoic acid", *Anal. Chem.*, vol. 58, pp. 1344-1348, 1986.

C.B. Clish et al., "Oxidoreductases in lipoxin $A_4$ metabolic inactivation", *J. Biol. Chem.*, vol. 375, pp. 25372-25380, 2000.

S.P. Colgan et al., "Lipoxin $A_4$ modulates transmigration of human neutrophils across intestinal epithelial monolayers", *J. Clin. Invest.*, vol. 92, pp. 75-82, 1993.

F.H. Qiu et al., "Aspirin-triggered lipoxin $A_4$ and lipoxin $A_4$ up-regulate transcriptional corepressor NAB1 in human neutrophils", *FASEB J.* 1096/ fj. 1001-0576fje, vol. 10, 2001.

S. Sawazaki et al., "Lipoxygenation of docosaxaenoic acid by the rate pineal body", *J. Neurochem.*, vol. 62, pp. 2437-2447, 1994.

C.C. Miller et al., "Dietary supplementation with ethyl ester concentrates of fish oil (n-3) and borage oil (n-6) polyunsaturated fatty acids induces epidermal generation of local putative anti-inflammatory metabolites", *J. Invest. Dermat.*, vol. 96, pp. 98-103, 1991.

E.J. Corey et al., "Docosahexaaenoic acid is a strong inhibitor of prostaglandin but not leukotriene biosynthesis", *Proc. Natl. Acad. Sci. USA*, vol. 80, pp. 3581-3584, 1983.

M.K. O'Banion et al., Cdna Cloning and functional activity of a glucocorticoid-regulated inflammatory cyclooxygenase, *Proc. Natl., Acad., Sci. USA*, vol. 89, pp. 4888-4892, 1992.

T. Shimizu et al., "Enzyme with dual lipooxygenase activities catalyzes luekotriene $A_4$ synthesis from arachidonic acid", *Proc. Natl. Acad. Sci. USA*, vol. 81, pp. 689-693, 1994.

V.A. Ziboth et al., "Metabolism of polyunsaturated fatty acids by skin epidermal enzymes: generation of anti-inflammatory and antiproliferative metabolites", Am. J. Clin. Nutr., vol. 71 (Suppl.), pp. 361S-366S, 2000.

N. Salem et al., "Arachidonic and docosahexaenoic acids are biosynthesized from their 18-carbon precursors in human infants", *Proc. Natl. Acad. Sci. USA*, vol. 93, pp. 49-54, 1996.

J. Tou, "Acylation of docosahexaenoic acid into phospholipids by by intact human neutrophils", *Lipids*, vol. 21, pp. 324-327, 1986.

J.S. Poling, et al., Docosahexaenoic acid block of neuronal voltage-gated K+ channels: subunit selective antagonism by zinc, *Neuropharmacology*, vol. 35, pp. 969-982, 1996.

A. Mata de Urquiza et al., "Docosahexaenoic acids, a ligand for the retinoid X receptor in mouse brain", *Science*, vol. 290, pp. 2140-2144, 2000.

S.D. Freeman et al., "Characterization of LPS-induced lung inflammation in cftr mice and the effect of docosahexaenoic acid", *J. Appl. Physiol.* vol. 92, pp. 2169-2176, 2002.

E.E. Reich et al., "Formation of novel D-ring and E-ring isoprostane-like compounds ($D_4/E_4$-neuroprostanes) in vivo from docosahexaenoic acid", *Biochemistry*, vol. 39, pp. 2376-2383, 2000.

G. Garcia-Cardena et al., "Biomechanical activation of cascular endothelium as a determinant of its functional phenotype", *Proc. Natl. Acad. Sci. USA*, vol. 98, pp. 4478-4485, 2001.

P.A. Gum et al., "Aspirin use and all-cause mortality among patients being valuated for known or suspected coronary artery disease: a propensity analysis", *J.A.M.A.*, vol. 286, pp. 1187-1194, 2001.

I.H. Rosenberg et al., "Fish-food to calm the heart", *N. Engl. J. Med.*, vol. 346, pp. 1102-1103, 2002.

J.F. Maddox et al., "Lipoxin $A_4$ and $B_4$ are potent stimuli for human monocyte migration and adhesion selective inactivation by dehydrogenation and reduction", *J. Exp. Med.*, vol. 183, pp. 137-146, 1996.

J.F. Schmedtje, Jr. et al., "Hypoxia Induces Cyclooxygenase-2 via the NF- Kb p65 Transcription Factor in Human Vascular Endothelial Cells", *J. Biol. Chem.*, vol. 272, No. 1 pp. 601-608, 1997.

ResoER1(Human)   1 MRMEDEDYNTSISYGDEYPDYLDSIVVLEDLSPLEARVTRIFLVVVYSIVCFLGILGNGL  60
ResoER1(Mouse)   1 -MEYDAYNDSGIYDDEYSDGFGYFVDLEEASPWEAKVAPVFLVVIYSLVCFLGLLGNGL  58
ResoER1(Rat)     1 -MEYEGYNDSSIYGEEYSDGSDYIVDLEEAGPLEAKVAEVFLVVIYSLVCFLGILGNGL  58
                      * * ** *   * ** * ** *  *    **   *** ***

61 VIIIATFKMKKTVNMVWFLNLAVADFLFNVFLPIHITYAAMDYHWVFGTAMCKISNFLLI 120
59 VIVIATFKMKKTVNTVWFVNLAVADFLFNIFLPMHITYAAMDYHWVFGKAMCKISNFLLS 118
59 VIVIATFKMKKTVNTVWFVNLAVADFLFNIFLPIHITYAAMDYHWVFGKAMCKISSFLLS 118
    ******* * ******* * ************** ** *

121 HNMFTSVFLLTIISSDRCISVLLPVWSQNHRSVRLAYMACMVIWVLAFFLSS-PSLVFRD 179
119 HNMYTSVFLLTVISFDRCISVLLPVWSQNHRSIRLAYMTCSAVWV-LAFFLSSPSLVFRD 177
119 HNMYTSVFLLTVISFDRCISVLLPVWSQNHRSVRLAYMTCVVVWVWLS-SESPPSLVFGH 177
    * ***  *************** **** *   **   *  * *****

180 TANLHGKISCFNNFSLSTPGSSSWPTHSQMDPVGYSRHMVVTVTRFLCGFLVPVLIITAC 239
178 TANIHGKITCFNNFSLAAPESSPHPAHSQVVSTGYSRHVAVTVTRFLCGFLIPVFIITAC 237
178 VSTSHGKITCFNNFSLAAPEPFSHSTHPRTDPVGYSRHVAVTVTRFLCGFLIPVFIITAC 237
        ** ****** * *       *    * ***** * *********  *****

240 YLTIVCKLQRNRLAKTKKPFKIIVTIIITFFLCWCPYHTLNLLELHHTAMPGSVFSLGLP 299
238 YLTIVFKLQRNRLAKNKKPFKIIITIIITFFLCWCPYHTLYLLELHHTAVPSSVFSLGLP 297
238 YLTIVFKLQRNRQAKTKKPFKIIITIIITFFLCWCPYHTLYLLELHHTAVPASVFSLGLP 297
    *** **  ***** ***********  ****** *  *******

300 LATALAIANSCMNPILYVFMGQDFKKFKVALFSRLVNALSEDTGHSSYPSHRSFTKMSSM 359
298 LATAVAIANSCMNPILYVFMGHDFRKFKVALFSRLANALSEDTGPSSYPSHRSFTKMSSL 357
298 LATAVAIANSCMNPILYVFMGHDFKKFKVALFSRLVNALSEDTGPSSYPSHRSFTKMSSL 357
    **  ***********  ******* **** **************

360 NERTSMNERETGML                      373
358 NEKASVNEKETSTL                      371
358 IEKASVNEKETSTL                      371
     *  *    *

|       | Human | Mouse | Rat  |
|-------|-------|-------|------|
| Human |       | 80.3  | 79.2 |
| Mouse |       |       | 87.6 |
| Rat   |       |       |      |

FIG. 11 human ResoER1 loop2  136 DRCISVLLPVWSQNHRSVRLA 156
mouse ResoER1 loop2  134 DRCISVLLPVWSQNHRSIRLA 154
rat   ResoER1 loop2  134 DRCISVLLPVWSQNHRSVRLA 154
human ALX    loop2  122 DRCICVLHPVWAQNHRTVSLA 142
                        **..*....

human ResoER1 TM7  301 ATA-LAIANSCMNPILYVFMGQDF 323
mouse ResoER1 TM7  299 ATA-VAIANSCMNPILYVFMGHDF 321
rat   ResoER1 TM7  299 ATA-VAIANSCMNPILYVFMGHDF 321
human ALX    TM7  287 -TSSLAFFNSCLNPMLYVFVGQDF 309

SEQUENCE LISTING

<160> NUMBER OF SEQ ID NOS: 33

<210> SEQ ID NO 1
<211> LENGTH: 373
<212> TYPE: PRT
<213> ORGANISM: HOMO SAPIENS

<400> SEQUENCE: 1

```
Met Arg Met Glu Asp Glu Asp Tyr Asn Thr Ser Ile Ser Tyr Gly Asp
 1               5                  10                  15

Glu Tyr Pro Asp Tyr Leu Asp Ser Ile Val Val Leu Glu Asp Leu Ser
             20                  25                  30

Pro Leu Glu Ala Arg Val Thr Arg Ile Phe Leu Val Val Val Tyr Ser
         35                  40                  45

Ile Val Cys Phe Leu Gly Ile Leu Gly Asn Gly Leu Val Ile Ile Ile
     50                  55                  60

Ala Thr Phe Lys Met Lys Lys Thr Val Asn Met Val Trp Phe Leu Asn
65                  70                  75                  80

Leu Ala Val Ala Asp Phe Leu Phe Asn Val Phe Leu Pro Ile His Ile
                 85                  90                  95

Thr Tyr Ala Ala Met Asp Tyr His Trp Val Phe Gly Thr Ala Met Cys
            100                 105                 110

Lys Ile Ser Asn Phe Leu Leu Ile His Asn Met Phe Thr Ser Val Phe
        115                 120                 125

Leu Leu Thr Ile Ile Ser Ser Asp Arg Cys Ile Ser Val Leu Leu Pro
    130                 135                 140

Val Trp Ser Gln Asn His Arg Ser Val Arg Leu Ala Tyr Met Ala Cys
145                 150                 155                 160

Met Val Ile Trp Val Leu Ala Phe Phe Leu Ser Ser Pro Ser Leu Val
                165                 170                 175

Phe Arg Asp Thr Ala Asn Leu His Gly Lys Ile Ser Cys Phe Asn Asn
            180                 185                 190

Phe Ser Leu Ser Thr Pro Gly Ser Ser Ser Trp Pro Thr His Ser Gln
        195                 200                 205

Met Asp Pro Val Gly Tyr Ser Arg His Met Val Val Thr Val Thr Arg
    210                 215                 220

Phe Leu Cys Gly Phe Leu Val Pro Val Leu Ile Ile Thr Ala Cys Tyr
225                 230                 235                 240

Leu Thr Ile Val Cys Lys Leu Gln Arg Asn Arg Leu Ala Lys Thr Lys
                245                 250                 255

Lys Pro Phe Lys Ile Ile Val Thr Ile Ile Ile Thr Phe Phe Leu Cys
            260                 265                 270

Trp Cys Pro Tyr His Thr Leu Asn Leu Leu Glu Leu His His Thr Ala
        275                 280                 285

Met Pro Gly Ser Val Phe Ser Leu Gly Leu Pro Leu Ala Thr Ala Leu
    290                 295                 300

Ala Ile Ala Asn Ser Cys Met Asn Pro Ile Leu Tyr Val Phe Met Gly
305                 310                 315                 320

Gln Asp Phe Lys Lys Phe Lys Val Ala Leu Phe Ser Arg Leu Val Asn
                325                 330                 335

Ala Leu Ser Glu Asp Thr Gly His Ser Ser Tyr Pro Ser His Arg Ser
            340                 345                 350

Phe Thr Lys Met Ser Ser Met Asn Glu Arg Thr Ser Met Asn Glu Arg
```

```
                355                 360                 365

Glu Thr Gly Met Leu
        370

<210> SEQ ID NO 2
<211> LENGTH: 371
<212> TYPE: PRT
<213> ORGANISM: MOUSE

<400> SEQUENCE: 2

Met Glu Tyr Asp Ala Tyr Asn Asp Ser Gly Ile Tyr Asp Asp Glu Tyr
1               5                   10                  15

Ser Asp Gly Phe Gly Tyr Phe Val Asp Leu Glu Glu Ala Ser Pro Trp
            20                  25                  30

Glu Ala Lys Val Ala Pro Val Phe Leu Val Val Ile Tyr Ser Leu Val
        35                  40                  45

Cys Phe Leu Gly Leu Leu Gly Asn Gly Leu Val Ile Val Ile Ala Thr
    50                  55                  60

Phe Lys Met Lys Lys Thr Val Asn Thr Val Trp Phe Val Asn Leu Ala
65                  70                  75                  80

Val Ala Asp Phe Leu Phe Asn Ile Phe Leu Pro Met His Ile Thr Tyr
                85                  90                  95

Ala Ala Met Asp Tyr His Trp Val Phe Gly Lys Ala Met Cys Lys Ile
            100                 105                 110

Ser Asn Phe Leu Leu Ser His Asn Met Tyr Thr Ser Val Phe Leu Leu
        115                 120                 125

Thr Val Ile Ser Phe Asp Arg Cys Ile Ser Val Leu Leu Pro Val Trp
    130                 135                 140

Ser Gln Asn His Arg Ser Ile Arg Leu Ala Tyr Met Thr Cys Ser Ala
145                 150                 155                 160

Val Trp Val Leu Ala Phe Phe Leu Ser Ser Pro Ser Leu Val Phe Arg
                165                 170                 175

Asp Thr Ala Asn Ile His Gly Lys Ile Thr Cys Phe Asn Asn Phe Ser
            180                 185                 190

Leu Ala Ala Pro Glu Ser Ser Pro His Pro Ala His Ser Gln Val Val
        195                 200                 205

Ser Thr Gly Tyr Ser Arg His Val Ala Val Thr Val Thr Arg Phe Leu
    210                 215                 220

Cys Gly Phe Leu Ile Pro Val Phe Ile Ile Thr Ala Cys Tyr Leu Thr
225                 230                 235                 240

Ile Val Phe Lys Leu Gln Arg Asn Arg Leu Ala Lys Asn Lys Lys Pro
                245                 250                 255

Phe Lys Ile Ile Ile Thr Ile Ile Thr Phe Phe Leu Cys Trp Cys
            260                 265                 270

Pro Tyr His Thr Leu Tyr Leu Leu Glu Leu His His Thr Ala Val Pro
        275                 280                 285

Ser Ser Val Phe Ser Leu Gly Leu Pro Leu Ala Thr Ala Val Ala Ile
    290                 295                 300

Ala Asn Ser Cys Met Asn Pro Ile Leu Tyr Val Phe Met Gly His Asp
305                 310                 315                 320

Phe Arg Lys Phe Lys Val Ala Leu Phe Ser Arg Leu Ala Asn Ala Leu
                325                 330                 335

Ser Glu Asp Thr Gly Pro Ser Ser Tyr Pro Ser His Arg Ser Phe Thr
            340                 345                 350
```

```
Lys Met Ser Ser Leu Asn Glu Lys Ala Ser Val Asn Glu Lys Glu Thr
            355                 360                 365
Ser Thr Leu
    370

<210> SEQ ID NO 3
<211> LENGTH: 371
<212> TYPE: PRT
<213> ORGANISM: RAT

<400> SEQUENCE: 3

Met Glu Tyr Glu Gly Tyr Asn Asp Ser Ser Ile Tyr Gly Glu Tyr
1               5                   10                  15

Ser Asp Gly Ser Asp Tyr Ile Val Asp Leu Glu Glu Ala Gly Pro Leu
            20                  25                  30

Glu Ala Lys Val Ala Glu Val Phe Leu Val Ile Tyr Ser Leu Val
            35                  40                  45

Cys Phe Leu Gly Ile Leu Gly Asn Gly Leu Val Ile Val Ile Ala Thr
    50                  55                  60

Phe Lys Met Lys Lys Thr Val Asn Thr Val Trp Phe Val Asn Leu Ala
65                  70                  75                  80

Val Ala Asp Phe Leu Phe Asn Ile Phe Leu Pro Ile His Ile Thr Tyr
                85                  90                  95

Ala Ala Met Asp Tyr His Trp Val Phe Gly Lys Ala Met Cys Lys Ile
            100                 105                 110

Ser Ser Phe Leu Leu Ser His Asn Met Tyr Thr Ser Val Phe Leu Leu
            115                 120                 125

Thr Val Ile Ser Phe Asp Arg Cys Ile Ser Val Leu Leu Pro Val Trp
    130                 135                 140

Ser Gln Asn His Arg Ser Val Arg Leu Ala Tyr Met Thr Cys Val Val
145                 150                 155                 160

Val Trp Val Trp Leu Ser Ser Glu Ser Pro Pro Ser Leu Val Phe Gly
                165                 170                 175

His Val Ser Thr Ser His Gly Lys Ile Thr Cys Phe Asn Asn Phe Ser
            180                 185                 190

Leu Ala Ala Pro Glu Pro Phe Ser His Ser Thr His Pro Arg Thr Asp
            195                 200                 205

Pro Val Gly Tyr Ser Arg His Val Ala Val Thr Val Thr Arg Phe Leu
    210                 215                 220

Cys Gly Phe Leu Ile Pro Val Phe Ile Ile Thr Ala Cys Tyr Leu Thr
225                 230                 235                 240

Ile Val Phe Lys Leu Gln Arg Asn Arg Gln Ala Lys Thr Lys Lys Pro
                245                 250                 255

Phe Lys Ile Ile Ile Thr Ile Ile Thr Phe Phe Leu Cys Trp Cys
            260                 265                 270

Pro Tyr His Thr Leu Tyr Leu Leu Glu Leu His His Thr Ala Val Pro
    275                 280                 285

Ala Ser Val Phe Ser Leu Gly Leu Pro Leu Ala Thr Ala Val Ala Ile
            290                 295                 300

Ala Asn Ser Cys Met Asn Pro Ile Leu Tyr Val Phe Met Gly His Asp
305                 310                 315                 320

Phe Lys Lys Phe Lys Val Ala Leu Phe Ser Arg Leu Val Asn Ala Leu
                325                 330                 335

Ser Glu Asp Thr Gly Pro Ser Ser Tyr Pro Ser His Arg Ser Phe Thr
            340                 345                 350
```

```
Lys Met Ser Ser Leu Ile Glu Lys Ala Ser Val Asn Glu Lys Glu Thr
            355                 360                 365
Ser Thr Leu
    370

<210> SEQ ID NO 4
<211> LENGTH: 21
<212> TYPE: PRT
<213> ORGANISM: HOMO SAPIENS

<400> SEQUENCE: 4

Asp Arg Cys Ile Ser Val Leu Leu Pro Val Trp Ser Gln Asn His Arg
1               5                   10                  15
Ser Val Arg Leu Ala
            20

<210> SEQ ID NO 5
<211> LENGTH: 21
<212> TYPE: PRT
<213> ORGANISM: MOUSE

<400> SEQUENCE: 5

Asp Arg Cys Ile Ser Val Leu Leu Pro Val Trp Ser Gln Asn His Arg
1               5                   10                  15
Ser Ile Arg Leu Ala
            20

<210> SEQ ID NO 6
<211> LENGTH: 21
<212> TYPE: PRT
<213> ORGANISM: RAT

<400> SEQUENCE: 6

Asp Arg Cys Ile Ser Val Leu Leu Pro Val Trp Ser Gln Asn His Arg
1               5                   10                  15
Ser Val Arg Leu Ala
            20

<210> SEQ ID NO 7
<211> LENGTH: 21
<212> TYPE: PRT
<213> ORGANISM: HOMO SAPIENS

<400> SEQUENCE: 7

Asp Arg Cys Ile Cys Val Leu His Pro Val Trp Ala Gln Asn His Arg
1               5                   10                  15
Thr Val Ser Leu Ala
            20

<210> SEQ ID NO 8
<211> LENGTH: 23
<212> TYPE: PRT
<213> ORGANISM: HOMO SAPIENS

<400> SEQUENCE: 8

Ala Thr Ala Leu Ala Ile Ala Asn Ser Cys Met Asn Pro Ile Leu Tyr
1               5                   10                  15
Val Phe Met Gly Gln Asp Phe
            20

<210> SEQ ID NO 9
```

```
<211> LENGTH: 23
<212> TYPE: PRT
<213> ORGANISM: MOUSE

<400> SEQUENCE: 9

Ala Thr Ala Val Ala Ile Ala Asn Ser Cys Met Asn Pro Ile Leu Tyr
1               5                   10                  15

Val Phe Met Gly His Asp Phe
            20

<210> SEQ ID NO 10
<211> LENGTH: 23
<212> TYPE: PRT
<213> ORGANISM: RAT

<400> SEQUENCE: 10

Ala Thr Ala Val Ala Ile Ala Asn Ser Cys Met Asn Pro Ile Leu Tyr
1               5                   10                  15

Val Phe Met Gly His Asp Phe
            20

<210> SEQ ID NO 11
<211> LENGTH: 23
<212> TYPE: PRT
<213> ORGANISM: HOMO SAPIENS

<400> SEQUENCE: 11

Thr Ser Ser Leu Ala Phe Phe Asn Ser Cys Leu Asn Pro Met Leu Tyr
1               5                   10                  15

Val Phe Val Gly Gln Asp Phe
            20

<210> SEQ ID NO 12
<211> LENGTH: 351
<212> TYPE: PRT
<213> ORGANISM: HOMO SAPIENS

<400> SEQUENCE: 12

Met Glu Thr Asn Phe Ser Thr Pro Leu Asn Glu Tyr Glu Glu Val Ser
1               5                   10                  15

Tyr Glu Ser Ala Gly Tyr Thr Val Leu Arg Ile Leu Pro Leu Val Val
                20                  25                  30

Leu Gly Val Thr Phe Val Leu Gly Val Leu Gly Asn Gly Leu Val Ile
            35                  40                  45

Trp Val Ala Gly Phe Arg Met Thr Arg Thr Val Thr Thr Ile Cys Tyr
50                  55                  60

Leu Asn Leu Ala Leu Ala Asp Phe Ser Phe Thr Ala Thr Leu Pro Phe
65                  70                  75                  80

Leu Ile Val Ser Met Ala Met Gly Glu Lys Trp Pro Phe Gly Trp Phe
                85                  90                  95

Leu Cys Lys Leu Ile His Ile Val Val Asp Ile Asn Leu Phe Gly Ser
            100                 105                 110

Val Phe Leu Ile Gly Phe Ile Ala Leu Asp Arg Cys Ile Cys Val Leu
        115                 120                 125

His Pro Val Trp Ala Gln Asn His Arg Thr Val Ser Leu Ala Met Lys
    130                 135                 140

Val Ile Val Gly Pro Trp Ile Leu Ala Leu Val Leu Thr Leu Pro Val
145                 150                 155                 160

Phe Leu Phe Leu Thr Thr Val Thr Ile Pro Asn Gly Asp Thr Tyr Cys
```

-continued

```
                      165                 170                 175
Thr Phe Asn Phe Ala Ser Trp Gly Gly Thr Pro Glu Glu Arg Leu Lys
            180                 185                 190

Val Ala Ile Thr Met Leu Thr Ala Arg Gly Ile Ile Arg Phe Val Ile
        195                 200                 205

Gly Phe Ser Leu Pro Met Ser Ile Val Ala Ile Cys Tyr Gly Leu Ile
    210                 215                 220

Ala Ala Lys Ile His Lys Lys Gly Met Ile Lys Ser Ser Arg Pro Leu
225                 230                 235                 240

Arg Val Leu Thr Ala Val Val Ala Ser Phe Phe Ile Cys Trp Phe Pro
                245                 250                 255

Phe Gln Leu Val Ala Leu Leu Gly Thr Val Trp Leu Lys Glu Met Leu
            260                 265                 270

Phe Tyr Gly Lys Tyr Lys Ile Ile Asp Ile Leu Val Asn Pro Thr Ser
        275                 280                 285

Ser Leu Ala Phe Phe Asn Ser Cys Leu Asn Pro Met Leu Tyr Val Phe
    290                 295                 300

Val Gly Gln Asp Phe Arg Glu Arg Leu Ile His Ser Leu Pro Thr Ser
305                 310                 315                 320

Leu Glu Arg Ala Leu Ser Glu Asp Ser Ala Pro Thr Asn Asp Thr Ala
                325                 330                 335

Ala Asn Ser Ala Ser Pro Pro Ala Glu Thr Glu Leu Gln Ala Met
            340                 345                 350
```

<210> SEQ ID NO 13
<211> LENGTH: 20
<212> TYPE: DNA
<213> ORGANISM: HOMO SAPIENS

<400> SEQUENCE: 13
atgagaatgg aggatgaaga                                              20

<210> SEQ ID NO 14
<211> LENGTH: 19
<212> TYPE: DNA
<213> ORGANISM: HOMO SAPIENS

<400> SEQUENCE: 14
tcaaagcatg ccggtctcc                                               19

<210> SEQ ID NO 15
<211> LENGTH: 20
<212> TYPE: DNA
<213> ORGANISM: MOUSE

<400> SEQUENCE: 15
atggagtacg acgcttacaa                                              20

<210> SEQ ID NO 16
<211> LENGTH: 23
<212> TYPE: DNA
<213> ORGANISM: MOUSE

<400> SEQUENCE: 16
tcagagggta ctggtctcct tct                                          23

<210> SEQ ID NO 17
<211> LENGTH: 24
<212> TYPE: DNA

```
<213> ORGANISM: MOUSE

<400> SEQUENCE: 17
gctgactatg gctacaaaag ctgg                                    24

<210> SEQ ID NO 18
<211> LENGTH: 24
<212> TYPE: DNA
<213> ORGANISM: MOUSE

<400> SEQUENCE: 18
atgctcaggg acttgaggag ggta                                    24

<210> SEQ ID NO 19
<211> LENGTH: 22
<212> TYPE: DNA
<213> ORGANISM: MOUSE

<400> SEQUENCE: 19
gaccacagtc catgacatca ct                                      22

<210> SEQ ID NO 20
<211> LENGTH: 21
<212> TYPE: DNA
<213> ORGANISM: MOUSE

<400> SEQUENCE: 20
tccaccaccc tgttgctgta g                                       21

<210> SEQ ID NO 21
<211> LENGTH: 25
<212> TYPE: DNA
<213> ORGANISM: MOUSE

<400> SEQUENCE: 21
aacacugugu gguuugucaa cdtdt                                   25

<210> SEQ ID NO 22
<211> LENGTH: 21
<212> TYPE: RNA
<213> ORGANISM: MOUSE

<400> SEQUENCE: 22
auuguaugcg aucgcagacu u                                       21

<210> SEQ ID NO 23
<211> LENGTH: 350
<212> TYPE: PRT
<213> ORGANISM: HOMO SAPIENS

<400> SEQUENCE: 23
```

Met Glu Thr Asn Ser Ser Leu Pro Thr Asn Ile Ser Gly Gly Thr Pro
1               5                   10                  15

Ala Val Ser Ala Gly Tyr Leu Phe Leu Asp Ile Ile Thr Tyr Leu Val
            20                  25                  30

Phe Ala Val Thr Phe Val Leu Gly Val Leu Gly Asn Gly Leu Val Ile
        35                  40                  45

Trp Val Ala Gly Phe Arg Met Thr His Thr Val Thr Thr Ile Ser Tyr
    50                  55                  60

Leu Asn Leu Ala Val Ala Asp Phe Cys Phe Thr Ser Thr Leu Pro Phe
65                  70                  75                  80

```
Phe Met Val Arg Lys Ala Met Gly Gly His Trp Pro Phe Gly Trp Phe
                85                  90                  95

Leu Cys Lys Phe Leu Phe Thr Ile Val Asp Ile Asn Leu Phe Gly Ser
            100                 105                 110

Val Phe Leu Ile Ala Leu Ile Ala Leu Asp Arg Cys Val Cys Val Leu
        115                 120                 125

His Pro Val Trp Thr Gln Asn His Arg Thr Val Ser Leu Ala Lys Lys
    130                 135                 140

Val Ile Ile Gly Pro Trp Val Met Ala Leu Leu Thr Leu Pro Val
145                 150                 155                 160

Ile Ile Arg Val Thr Thr Val Pro Gly Lys Thr Gly Thr Val Ala Cys
                165                 170                 175

Thr Phe Asn Phe Ser Pro Trp Thr Asn Asp Pro Lys Glu Arg Ile Asn
            180                 185                 190

Val Ala Val Ala Met Leu Thr Val Arg Gly Ile Ile Arg Phe Ile Ile
        195                 200                 205

Gly Phe Ser Ala Pro Met Ser Ile Val Ala Val Ser Tyr Gly Leu Ile
    210                 215                 220

Ala Thr Lys Ile His Lys Gln Gly Leu Ile Lys Ser Ser Arg Pro Leu
225                 230                 235                 240

Arg Val Leu Ser Phe Val Ala Ala Ala Phe Phe Leu Cys Trp Ser Pro
                245                 250                 255

Tyr Gln Val Val Ala Leu Ile Ala Thr Val Arg Ile Arg Glu Leu Leu
            260                 265                 270

Gln Gly Met Tyr Lys Glu Ile Gly Ile Ala Val Asp Val Thr Ser Ala
        275                 280                 285

Leu Ala Phe Phe Asn Ser Cys Leu Asn Pro Met Leu Tyr Val Phe Met
    290                 295                 300

Gly Gln Asp Phe Arg Glu Arg Leu Ile His Ala Leu Pro Ala Ser Leu
305                 310                 315                 320

Glu Arg Ala Leu Thr Glu Asp Ser Thr Gln Thr Ser Asp Thr Ala Thr
                325                 330                 335

Asn Ser Thr Leu Pro Ser Ala Glu Val Ala Leu Gln Ala Lys
            340                 345                 350

<210> SEQ ID NO 24
<211> LENGTH: 351
<212> TYPE: PRT
<213> ORGANISM: HOMO SAPIENS

<400> SEQUENCE: 24

Met Glu Thr Asn Phe Ser Thr Pro Leu Asn Glu Tyr Glu Glu Val Ser
1               5                   10                  15

Tyr Glu Ser Ala Gly Tyr Thr Val Leu Arg Ile Leu Pro Leu Val Val
            20                  25                  30

Leu Gly Val Thr Phe Val Leu Gly Val Leu Gly Asn Gly Leu Val Ile
        35                  40                  45

Trp Val Ala Gly Phe Arg Met Thr Arg Thr Val Thr Thr Ile Cys Tyr
    50                  55                  60

Leu Asn Leu Ala Leu Ala Asp Phe Ser Phe Thr Ala Thr Leu Pro Phe
65                  70                  75                  80

Leu Ile Val Ser Met Ala Met Gly Glu Lys Trp Pro Phe Gly Trp Phe
                85                  90                  95

Leu Cys Lys Leu Ile His Ile Val Val Asp Ile Asn Leu Phe Gly Ser
            100                 105                 110
```

```
Val Phe Leu Ile Gly Phe Ile Ala Leu Asp Arg Cys Ile Cys Val Leu
            115                 120                 125

His Pro Val Trp Ala Gln Asn His Arg Thr Val Ser Leu Ala Met Lys
    130                 135                 140

Val Ile Val Gly Pro Trp Ile Leu Ala Leu Val Leu Thr Leu Pro Val
145                 150                 155                 160

Phe Leu Phe Leu Thr Thr Val Thr Ile Pro Asn Gly Asp Thr Tyr Cys
                165                 170                 175

Thr Phe Asn Phe Ala Ser Trp Gly Gly Thr Pro Glu Glu Arg Leu Lys
            180                 185                 190

Val Ala Ile Thr Met Leu Thr Ala Arg Gly Ile Ile Arg Phe Val Ile
        195                 200                 205

Gly Phe Ser Leu Pro Met Ser Ile Val Ala Ile Cys Tyr Gly Leu Ile
    210                 215                 220

Ala Ala Lys Ile His Lys Lys Gly Met Ile Lys Ser Ser Arg Pro Leu
225                 230                 235                 240

Arg Val Leu Thr Ala Val Val Ala Ser Phe Phe Ile Cys Trp Phe Pro
                245                 250                 255

Phe Gln Leu Val Ala Leu Leu Gly Thr Val Trp Leu Lys Glu Met Leu
            260                 265                 270

Phe Tyr Gly Lys Tyr Lys Ile Ile Asp Ile Leu Val Asn Pro Thr Ser
        275                 280                 285

Ser Leu Ala Phe Phe Asn Ser Cys Leu Asn Pro Met Leu Tyr Val Phe
    290                 295                 300

Val Gly Gln Asp Phe Arg Glu Arg Leu Ile His Ser Leu Pro Thr Ser
305                 310                 315                 320

Leu Glu Arg Ala Leu Ser Glu Asp Ser Ala Pro Thr Asn Asp Thr Ala
                325                 330                 335

Ala Asn Ser Ala Ser Pro Pro Ala Glu Thr Glu Leu Gln Ala Met
            340                 345                 350

<210> SEQ ID NO 25
<211> LENGTH: 353
<212> TYPE: PRT
<213> ORGANISM: HOMO SAPIENS

<400> SEQUENCE: 25

Met Glu Thr Asn Phe Ser Ile Pro Leu Asn Glu Thr Glu Glu Val Leu
1               5                   10                  15

Pro Glu Pro Ala Gly His Thr Val Leu Trp Ile Phe Ser Leu Leu Val
            20                  25                  30

His Gly Val Thr Phe Val Phe Gly Val Leu Gly Asn Gly Leu Val Ile
        35                  40                  45

Trp Val Ala Gly Phe Arg Met Thr Arg Thr Val Asn Thr Ile Cys Tyr
    50                  55                  60

Leu Asn Leu Ala Leu Ala Asp Phe Ser Phe Ser Ala Ile Leu Pro Phe
65                  70                  75                  80

Arg Met Val Ser Val Ala Met Arg Glu Lys Trp Pro Phe Gly Ser Phe
                85                  90                  95

Leu Cys Lys Leu Val His Val Met Ile Asp Ile Asn Leu Phe Val Ser
            100                 105                 110

Val Tyr Leu Ile Thr Ile Ile Ala Leu Asp Arg Cys Ile Cys Val Leu
        115                 120                 125

His Pro Ala Trp Ala Gln Asn His Arg Thr Met Ser Leu Ala Lys Arg
```

```
            130                 135                 140
Val Met Thr Gly Leu Trp Ile Phe Thr Ile Val Leu Thr Leu Pro Asn
145                 150                 155                 160

Phe Ile Phe Trp Thr Thr Ile Ser Thr Thr Asn Gly Asp Thr Tyr Cys
                165                 170                 175

Ile Phe Asn Phe Ala Phe Trp Gly Asp Thr Ala Val Glu Arg Leu Asn
            180                 185                 190

Val Phe Ile Thr Met Ala Lys Val Phe Leu Ile Leu His Phe Ile Ile
                195                 200                 205

Gly Phe Ser Val Pro Met Ser Ile Ile Thr Val Cys Tyr Gly Ile Ile
210                 215                 220

Ala Ala Lys Ile His Arg Asn His Met Ile Lys Ser Ser Arg Pro Leu
225                 230                 235                 240

Arg Val Phe Ala Ala Val Val Ala Ser Phe Phe Ile Cys Trp Phe Pro
                245                 250                 255

Tyr Glu Leu Ile Gly Ile Leu Met Ala Val Trp Leu Lys Glu Met Leu
                260                 265                 270

Leu Asn Gly Lys Tyr Lys Ile Ile Leu Val Leu Ile Asn Pro Thr Ser
                275                 280                 285

Ser Leu Ala Phe Phe Asn Ser Cys Leu Asn Pro Ile Leu Tyr Val Phe
290                 295                 300

Met Gly Arg Asn Phe Gln Glu Arg Leu Ile Arg Ser Leu Pro Thr Ser
305                 310                 315                 320

Leu Glu Arg Ala Leu Thr Glu Val Pro Asp Ser Ala Gln Thr Ser Asn
                325                 330                 335

Thr Asp Thr Thr Ser Ala Ser Pro Pro Glu Glu Thr Glu Leu Gln Ala
                340                 345                 350

Met

<210> SEQ ID NO 26
<211> LENGTH: 355
<212> TYPE: PRT
<213> ORGANISM: HOMO SAPIENS

<400> SEQUENCE: 26

Met Glu Asp Leu Glu Glu Thr Leu Phe Glu Glu Phe Glu Asn Tyr Ser
1               5                   10                  15

Tyr Asp Leu Asp Tyr Tyr Ser Leu Glu Ser Asp Leu Glu Glu Lys Val
                20                  25                  30

Gln Leu Gly Val Val His Trp Val Ser Leu Val Leu Tyr Cys Leu Ala
            35                  40                  45

Phe Val Leu Gly Ile Pro Gly Asn Ala Ile Val Ile Trp Phe Thr Gly
        50                  55                  60

Leu Lys Trp Lys Lys Thr Val Thr Thr Leu Trp Phe Leu Asn Leu Ala
65                  70                  75                  80

Ile Ala Asp Phe Ile Phe Leu Leu Phe Leu Pro Leu Tyr Ile Ser Tyr
                85                  90                  95

Val Ala Met Asn Phe His Trp Pro Phe Gly Ile Trp Leu Cys Lys Ala
                100                 105                 110

Asn Ser Phe Thr Ala Gln Leu Asn Met Phe Ala Ser Val Phe Phe Leu
            115                 120                 125

Thr Val Ile Ser Leu Asp His Tyr Ile His Leu Ile His Pro Val Leu
        130                 135                 140

Ser His Arg His Arg Thr Leu Lys Asn Ser Leu Ile Val Ile Ile Phe
```

```
                145                 150                 155                 160
Ile Trp Leu Leu Ala Ser Leu Ile Gly Gly Pro Ala Leu Tyr Phe Arg
                165                 170                 175

Asp Thr Val Glu Phe Asn Asn His Thr Leu Cys Tyr Asn Asn Phe Gln
            180                 185                 190

Lys His Asp Pro Asp Leu Thr Leu Ile Arg His His Val Leu Thr Trp
        195                 200                 205

Val Lys Phe Ile Ile Gly Tyr Leu Phe Pro Leu Leu Thr Met Ser Ile
    210                 215                 220

Cys Tyr Leu Cys Leu Ile Phe Lys Val Lys Lys Arg Thr Val Leu Ile
225                 230                 235                 240

Ser Ser Arg His Phe Trp Thr Ile Leu Val Val Val Ala Phe Val
            245                 250                 255

Val Cys Trp Thr Pro Tyr His Leu Phe Ser Ile Trp Glu Leu Thr Ile
            260                 265                 270

His His Asn Ser Tyr Ser His His Val Met Gln Ala Gly Ile Pro Leu
            275                 280                 285

Ser Thr Gly Leu Ala Phe Leu Asn Ser Cys Leu Asn Pro Ile Leu Tyr
        290                 295                 300

Val Leu Ile Ser Lys Lys Phe Gln Ala Arg Phe Arg Ser Ser Val Ala
305                 310                 315                 320

Glu Ile Leu Lys Tyr Thr Leu Trp Glu Val Ser Cys Ser Gly Thr Val
                325                 330                 335

Ser Glu Gln Leu Arg Asn Ser Glu Thr Lys Asn Leu Cys Leu Leu Glu
            340                 345                 350

Thr Ala Gln
        355

<210> SEQ ID NO 27
<211> LENGTH: 356
<212> TYPE: PRT
<213> ORGANISM: HOMO SAPIENS

<400> SEQUENCE: 27

Met Asn Gly Val Ser Glu Gly Thr Arg Gly Cys Ser Asp Arg Gln Pro
1               5                   10                  15

Gly Val Leu Thr Arg Asp Arg Ser Cys Ser Arg Lys Met Asn Ser Ser
            20                  25                  30

Gly Cys Leu Ser Glu Glu Val Gly Ser Leu Arg Pro Leu Thr Val Val
        35                  40                  45

Ile Leu Ser Ala Ser Ile Val Val Gly Val Leu Gly Asn Gly Leu Val
    50                  55                  60

Leu Trp Met Thr Val Phe Arg Met Ala Arg Thr Val Ser Thr Val Cys
65                  70                  75                  80

Phe Phe His Leu Ala Leu Ala Asp Phe Met Leu Ser Leu Ser Leu Pro
                85                  90                  95

Ile Ala Met Tyr Tyr Ile Val Ser Arg Gln Trp Leu Leu Gly Glu Trp
            100                 105                 110

Ala Cys Lys Leu Tyr Ile Thr Phe Val Phe Leu Ser Tyr Phe Ala Ser
        115                 120                 125

Asn Cys Leu Leu Val Phe Ile Ser Val Asp Arg Cys Ile Ser Val Leu
    130                 135                 140

Tyr Pro Val Trp Ala Leu Asn His Arg Thr Val Gln Arg Ala Ser Trp
145                 150                 155                 160
```

```
Leu Ala Phe Gly Val Trp Leu Ala Ala Ala Leu Cys Ser Ala His
                165                 170                 175

Leu Lys Phe Arg Thr Thr Arg Lys Trp Asn Gly Cys Thr His Cys Tyr
                180                 185                 190

Leu Ala Phe Asn Ser Asp Asn Glu Thr Ala Gln Ile Trp Ile Glu Gly
                195                 200                 205

Val Val Glu Gly His Ile Ile Gly Thr Ile Gly His Phe Leu Leu Gly
            210                 215                 220

Phe Leu Gly Pro Leu Ala Ile Ile Gly Thr Cys Ala His Leu Ile Arg
225                 230                 235                 240

Ala Lys Leu Leu Arg Glu Gly Trp Val His Ala Asn Arg Pro Lys Arg
                245                 250                 255

Leu Leu Leu Val Leu Val Ser Ala Phe Phe Ile Phe Trp Ser Pro Phe
                260                 265                 270

Asn Val Val Leu Leu Val His Leu Trp Arg Arg Val Met Leu Lys Glu
            275                 280                 285

Ile Tyr His Pro Arg Met Leu Leu Ile Leu Gln Ala Ser Phe Ala Leu
            290                 295                 300

Gly Cys Val Asn Ser Ser Leu Asn Pro Phe Leu Tyr Val Phe Val Gly
305                 310                 315                 320

Arg Asp Phe Gln Glu Lys Phe Phe Gln Ser Leu Thr Ser Ala Leu Ala
                325                 330                 335

Arg Ala Phe Gly Glu Glu Phe Leu Ser Ser Cys Pro Arg Gly Asn
                340                 345                 350

Ala Pro Arg Glu
            355

<210> SEQ ID NO 28
<211> LENGTH: 373
<212> TYPE: PRT
<213> ORGANISM: HOMO SAPIENS

<400> SEQUENCE: 28

Met Arg Met Glu Asp Glu Asp Tyr Asn Thr Ser Ile Ser Tyr Gly Asp
1               5                   10                  15

Glu Tyr Pro Asp Tyr Leu Asp Ser Ile Val Val Leu Glu Asp Leu Ser
                20                  25                  30

Pro Leu Glu Ala Arg Val Thr Arg Ile Phe Leu Val Val Val Tyr Ser
                35                  40                  45

Ile Val Cys Phe Leu Gly Ile Leu Gly Asn Gly Leu Val Ile Ile Ile
            50                  55                  60

Ala Thr Phe Lys Met Lys Lys Thr Val Asn Met Val Trp Phe Leu Asn
65              70                  75                  80

Leu Ala Val Ala Asp Phe Leu Phe Asn Val Phe Leu Pro Ile His Ile
                85                  90                  95

Thr Tyr Ala Ala Met Asp Tyr His Trp Val Phe Gly Thr Ala Met Cys
                100                 105                 110

Lys Ile Ser Asn Phe Leu Leu Ile His Asn Met Phe Thr Ser Val Phe
                115                 120                 125

Leu Leu Thr Ile Ile Ser Ser Asp Arg Cys Ile Ser Val Leu Leu Pro
            130                 135                 140

Val Trp Ser Gln Asn His Arg Ser Val Arg Leu Ala Tyr Met Ala Cys
145             150                 155                 160

Met Val Ile Trp Val Leu Ala Phe Phe Leu Ser Ser Pro Ser Leu Val
                165                 170                 175
```

```
Phe Arg Asp Thr Ala Asn Leu His Gly Lys Ile Ser Cys Phe Asn Asn
            180                 185                 190

Phe Ser Leu Ser Thr Pro Gly Ser Ser Ser Trp Pro Thr His Ser Gln
        195                 200                 205

Met Asp Pro Val Gly Tyr Ser Arg His Met Val Thr Val Thr Arg
    210                 215                 220

Phe Leu Cys Gly Phe Leu Val Pro Val Leu Ile Ile Thr Ala Cys Tyr
225                 230                 235                 240

Leu Thr Ile Val Cys Lys Leu Gln Arg Asn Arg Leu Ala Lys Thr Lys
                245                 250                 255

Lys Pro Phe Lys Ile Val Thr Ile Ile Thr Phe Phe Leu Cys
                260                 265                 270

Trp Cys Pro Tyr His Thr Leu Asn Leu Leu Glu Leu His His Thr Ala
            275                 280                 285

Met Pro Gly Ser Val Phe Ser Leu Gly Leu Pro Leu Ala Thr Ala Leu
        290                 295                 300

Ala Ile Ala Asn Ser Cys Met Asn Pro Ile Leu Tyr Val Phe Met Gly
305                 310                 315                 320

Gln Asp Phe Lys Lys Phe Lys Val Ala Leu Phe Ser Arg Leu Val Asn
                325                 330                 335

Ala Leu Ser Glu Asp Thr Gly His Ser Ser Tyr Pro Ser His Arg Ser
                340                 345                 350

Phe Thr Lys Met Ser Ser Met Asn Glu Arg Thr Ser Met Asn Glu Arg
                355                 360                 365

Glu Thr Gly Met Leu
        370

<210> SEQ ID NO 29
<211> LENGTH: 395
<212> TYPE: PRT
<213> ORGANISM: HOMO SAPIENS

<400> SEQUENCE: 29

Met Ser Ala Asn Ala Thr Leu Lys Pro Leu Cys Pro Ile Leu Glu Gln
1               5                   10                  15

Met Ser Arg Leu Gln Ser His Ser Asn Thr Ser Ile Arg Tyr Ile Asp
            20                  25                  30

His Ala Ala Val Leu Leu His Gly Leu Ala Ser Leu Leu Gly Leu Val
        35                  40                  45

Glu Asn Gly Val Ile Leu Phe Val Val Gly Cys Arg Met Arg Gln Thr
50                  55                  60

Val Val Thr Thr Trp Val Leu His Leu Ala Leu Ser Asp Leu Leu Ala
65                  70                  75                  80

Ser Ala Ser Leu Pro Phe Phe Thr Tyr Phe Leu Ala Val Gly His Ser
                85                  90                  95

Trp Glu Leu Gly Thr Thr Phe Cys Lys Leu His Ser Ser Ile Phe Phe
            100                 105                 110

Leu Asn Met Phe Ala Ser Gly Phe Leu Leu Ser Ala Ile Ser Leu Asp
            115                 120                 125

Arg Cys Leu Gln Val Val Arg Pro Val Trp Ala Gln Asn His Arg Thr
        130                 135                 140

Val Ala Ala Ala His Lys Val Cys Leu Val Leu Trp Ala Leu Ala Val
145                 150                 155                 160

Leu Asn Thr Val Pro Tyr Phe Val Phe Arg Asp Thr Ile Ser Arg Leu
```

-continued

```
                165                 170                 175
Asp Gly Arg Ile Met Cys Tyr Tyr Asn Val Leu Leu Leu Asn Pro Gly
            180                 185                 190

Pro Asp Arg Asp Ala Thr Cys Asn Ser Arg Gln Ala Ala Leu Ala Val
        195                 200                 205

Ser Lys Phe Leu Leu Ala Phe Leu Val Pro Leu Ala Ile Ile Ala Ser
    210                 215                 220

Ser His Ala Ala Val Ser Leu Arg Leu Gln His Arg Gly Arg Arg
225                 230                 235                 240

Pro Gly Arg Phe Val Arg Leu Val Ala Ala Val Ala Ala Phe Ala
                245                 250                 255

Leu Cys Trp Gly Pro Tyr His Val Phe Ser Leu Leu Glu Ala Arg Ala
            260                 265                 270

His Ala Asn Pro Gly Leu Arg Pro Leu Val Trp Arg Gly Leu Pro Phe
        275                 280                 285

Val Thr Ser Leu Ala Phe Phe Asn Ser Val Ala Asn Pro Val Leu Tyr
    290                 295                 300

Val Leu Thr Cys Pro Asp Met Leu Arg Lys Leu Arg Arg Ser Leu Arg
305                 310                 315                 320

Thr Val Leu Glu Ser Val Leu Val Asp Asp Ser Glu Leu Gly Gly Ala
                325                 330                 335

Gly Ser Ser Arg Arg Arg Thr Ser Ser Thr Ala Arg Ser Ala Ser
            340                 345                 350

Pro Leu Ala Leu Cys Ser Arg Pro Glu Glu Pro Arg Gly Pro Ala Arg
        355                 360                 365

Leu Leu Gly Trp Leu Leu Gly Ser Cys Ala Ala Ser Pro Gln Thr Gly
    370                 375                 380

Pro Leu Asn Arg Ala Leu Ser Ser Thr Ser Ser
385                 390                 395

<210> SEQ ID NO 30
<211> LENGTH: 482
<212> TYPE: PRT
<213> ORGANISM: HOMO SAPIENS

<400> SEQUENCE: 30

Met Ala Ser Phe Ser Ala Glu Thr Asn Ser Thr Asp Leu Leu Ser Gln
1               5                   10                  15

Pro Trp Asn Glu Pro Pro Val Ile Leu Ser Met Val Ile Leu Ser Leu
            20                  25                  30

Thr Phe Leu Leu Gly Leu Pro Gly Asn Gly Leu Val Leu Trp Val Ala
        35                  40                  45

Gly Leu Lys Met Gln Arg Thr Val Asn Thr Ile Trp Phe Leu His Leu
    50                  55                  60

Thr Leu Ala Asp Leu Leu Cys Cys Leu Ser Leu Pro Phe Ser Leu Ala
65                  70                  75                  80

His Leu Ala Leu Gln Gly Gln Trp Pro Tyr Gly Arg Phe Leu Cys Lys
                85                  90                  95

Leu Ile Pro Ser Ile Ile Val Leu Asn Met Phe Ala Ser Val Phe Leu
            100                 105                 110

Leu Thr Ala Ile Ser Leu Asp Arg Cys Leu Val Val Phe Lys Pro Ile
        115                 120                 125

Trp Cys Gln Asn His Arg Asn Val Gly Met Ala Cys Ser Ile Cys Gly
    130                 135                 140
```

```
Cys Ile Trp Val Val Ala Phe Val Met Cys Ile Pro Val Phe Val Tyr
145                 150                 155                 160

Arg Glu Ile Phe Thr Thr Asp Asn His Asn Arg Cys Gly Tyr Lys Phe
                165                 170                 175

Gly Leu Ser Ser Ser Leu Asp Tyr Pro Asp Phe Tyr Gly Asp Pro Leu
            180                 185                 190

Glu Asn Arg Ser Leu Glu Asn Ile Val Gln Pro Pro Gly Glu Met Asn
        195                 200                 205

Asp Arg Leu Asp Pro Ser Ser Phe Gln Thr Asn Asp His Pro Trp Thr
    210                 215                 220

Val Pro Thr Val Phe Gln Pro Gln Thr Phe Gln Arg Pro Ser Ala Asp
225                 230                 235                 240

Ser Leu Pro Arg Gly Ser Ala Arg Leu Thr Ser Gln Asn Leu Tyr Ser
                245                 250                 255

Asn Val Phe Lys Pro Ala Asp Val Val Ser Pro Lys Ile Pro Ser Gly
                260                 265                 270

Phe Pro Ile Glu Asp His Glu Thr Ser Pro Leu Asp Asn Ser Asp Ala
            275                 280                 285

Phe Leu Ser Thr His Leu Lys Leu Phe Pro Ser Ala Ser Ser Asn Ser
        290                 295                 300

Phe Tyr Glu Ser Glu Leu Pro Gln Gly Phe Gln Asp Tyr Tyr Asn Leu
305                 310                 315                 320

Gly Gln Phe Thr Asp Asp Gln Val Pro Thr Pro Leu Val Ala Ile
                325                 330                 335

Thr Ile Thr Arg Leu Val Val Gly Phe Leu Leu Pro Ser Val Ile Met
                340                 345                 350

Ile Ala Cys Tyr Ser Phe Ile Val Phe Arg Met Gln Arg Gly Arg Phe
                355                 360                 365

Ala Lys Ser Gln Ser Lys Thr Phe Arg Val Ala Val Val Val Val Ala
            370                 375                 380

Val Phe Leu Val Cys Trp Thr Pro Tyr His Ile Phe Gly Val Leu Ser
385                 390                 395                 400

Leu Leu Thr Asp Pro Glu Thr Pro Leu Gly Lys Thr Leu Met Ser Trp
                405                 410                 415

Asp His Val Cys Ile Ala Leu Ala Ser Ala Asn Ser Cys Phe Asn Pro
                420                 425                 430

Phe Leu Tyr Ala Leu Leu Gly Lys Asp Phe Arg Lys Lys Ala Arg Gln
            435                 440                 445

Ser Ile Gln Gly Ile Leu Glu Ala Ala Phe Ser Glu Glu Leu Thr Arg
        450                 455                 460

Ser Thr His Cys Pro Ser Asn Asn Val Ile Ser Glu Arg Asn Ser Thr
465                 470                 475                 480

Thr Val

<210> SEQ ID NO 31
<211> LENGTH: 350
<212> TYPE: PRT
<213> ORGANISM: HOMO SAPIENS

<400> SEQUENCE: 31

Met Asn Ser Phe Asn Tyr Thr Thr Pro Asp Tyr Gly His Tyr Asp Asp
1               5                   10                  15

Lys Asp Thr Leu Asp Leu Asn Thr Pro Val Asp Lys Thr Ser Asn Thr
            20                  25                  30
```

```
Leu Arg Val Pro Asp Ile Leu Ala Leu Val Ile Phe Ala Val Val Phe
        35                  40                  45

Leu Val Gly Val Leu Gly Asn Ala Leu Val Val Trp Val Thr Ala Phe
    50                  55                  60

Glu Ala Lys Arg Thr Ile Asn Ala Ile Trp Phe Leu Asn Leu Ala Val
65                  70                  75                  80

Ala Asp Phe Leu Ser Cys Leu Ala Leu Pro Ile Leu Phe Thr Ser Ile
                85                  90                  95

Val Gln His His His Trp Pro Phe Gly Gly Ala Ala Cys Ser Ile Leu
            100                 105                 110

Pro Ser Leu Ile Leu Leu Asn Met Tyr Ala Ser Ile Leu Leu Leu Ala
        115                 120                 125

Thr Ile Ser Ala Asp Arg Phe Leu Leu Val Phe Lys Pro Ile Trp Cys
    130                 135                 140

Gln Asn Phe Arg Gly Ala Gly Leu Ala Trp Ile Ala Cys Ala Val Ala
145                 150                 155                 160

Trp Gly Leu Ala Leu Leu Leu Thr Ile Pro Ser Phe Leu Tyr Arg Val
                165                 170                 175

Val Arg Glu Glu Tyr Phe Pro Pro Lys Val Leu Cys Gly Val Asp Tyr
            180                 185                 190

Ser His Asp Lys Arg Arg Glu Arg Ala Val Ala Ile Val Arg Leu Val
        195                 200                 205

Leu Gly Phe Leu Trp Pro Leu Leu Thr Leu Thr Ile Cys Tyr Thr Phe
    210                 215                 220

Ile Leu Leu Arg Thr Trp Ser Arg Arg Ala Thr Arg Ser Thr Lys Thr
225                 230                 235                 240

Leu Lys Val Val Ala Val Val Ala Ser Phe Phe Ile Phe Trp Leu
                245                 250                 255

Pro Tyr Gln Val Thr Gly Ile Met Met Ser Phe Leu Glu Pro Ser Ser
            260                 265                 270

Pro Thr Phe Leu Leu Leu Asn Lys Leu Asp Ser Leu Cys Val Ser Phe
        275                 280                 285

Ala Tyr Ile Asn Cys Cys Ile Asn Pro Ile Ile Tyr Val Val Ala Gly
    290                 295                 300

Gln Gly Phe Gln Gly Arg Leu Arg Lys Ser Leu Pro Ser Leu Leu Arg
305                 310                 315                 320

Asn Val Leu Thr Glu Glu Ser Val Val Arg Glu Ser Lys Ser Phe Thr
                325                 330                 335

Arg Ser Thr Val Asp Thr Met Ala Gln Lys Thr Gln Ala Val
            340                 345                 350

<210> SEQ ID NO 32
<211> LENGTH: 352
<212> TYPE: PRT
<213> ORGANISM: HOMO SAPIENS

<400> SEQUENCE: 32

Met Asn Thr Thr Ser Ser Ala Ala Pro Pro Ser Leu Gly Val Glu Phe
1               5                   10                  15

Ile Ser Leu Leu Ala Ile Ile Leu Leu Ser Val Ala Leu Ala Val Gly
            20                  25                  30

Leu Pro Gly Asn Ser Phe Val Val Trp Ser Ile Leu Lys Arg Met Gln
        35                  40                  45

Lys Arg Ser Val Thr Ala Leu Met Val Leu Asn Leu Ala Leu Ala Asp
    50                  55                  60
```

```
Leu Ala Val Leu Leu Thr Ala Pro Phe Phe Leu His Phe Leu Ala Gln
 65                  70                  75                  80

Gly Thr Trp Ser Phe Gly Leu Ala Gly Cys Arg Leu Cys His Tyr Val
                 85                  90                  95

Cys Gly Val Ser Met Tyr Ala Ser Val Leu Leu Ile Thr Ala Met Ser
            100                 105                 110

Leu Asp Arg Ser Leu Ala Val Ala Arg Pro Phe Val Ser Gln Lys Leu
            115                 120                 125

Arg Thr Lys Ala Met Ala Arg Arg Val Leu Ala Gly Ile Trp Val Leu
        130                 135                 140

Ser Phe Leu Leu Ala Thr Pro Val Leu Ala Tyr Arg Thr Val Val Pro
145                 150                 155                 160

Trp Lys Thr Asn Met Ser Leu Cys Phe Pro Arg Tyr Pro Ser Glu Gly
                165                 170                 175

His Arg Ala Phe His Leu Ile Phe Glu Ala Val Thr Gly Phe Leu Leu
            180                 185                 190

Pro Phe Leu Ala Val Val Ala Ser Tyr Ser Asp Ile Gly Arg Arg Leu
        195                 200                 205

Gln Ala Arg Arg Phe Arg Arg Ser Arg Arg Thr Gly Arg Leu Val Val
    210                 215                 220

Leu Ile Ile Leu Thr Phe Ala Ala Phe Trp Leu Pro Tyr His Val Val
225                 230                 235                 240

Asn Leu Ala Glu Ala Gly Arg Ala Leu Ala Gly Gln Ala Ala Gly Leu
                245                 250                 255

Gly Leu Val Gly Lys Arg Leu Ser Leu Ala Arg Asn Val Leu Ile Ala
            260                 265                 270

Leu Ala Phe Leu Ser Ser Ser Val Asn Pro Val Leu Tyr Ala Cys Ala
        275                 280                 285

Gly Gly Gly Leu Leu Arg Ser Ala Gly Val Gly Phe Val Ala Lys Leu
    290                 295                 300

Leu Glu Gly Thr Gly Ser Glu Ala Ser Ser Thr Arg Arg Gly Gly Ser
305                 310                 315                 320

Leu Gly Gln Thr Ala Arg Ser Gly Pro Ala Ala Leu Glu Pro Gly Pro
                325                 330                 335

Ser Glu Ser Leu Thr Ala Ser Ser Pro Leu Lys Leu Asn Glu Leu Asn
            340                 345                 350

<210> SEQ ID NO 33
<211> LENGTH: 371
<212> TYPE: PRT
<213> ORGANISM: MOUSE

<400> SEQUENCE: 33

Met Glu Tyr Asp Ala Tyr Asn Asp Ser Gly Ile Tyr Asp Asp Glu Tyr
  1               5                  10                  15

Ser Asp Gly Phe Gly Tyr Phe Val Asp Leu Glu Glu Ala Ser Pro Trp
                 20                  25                  30

Glu Ala Lys Val Ala Pro Val Phe Leu Val Val Ile Tyr Ser Leu Val
             35                  40                  45

Cys Phe Leu Gly Leu Leu Gly Asn Gly Leu Val Ile Val Ile Ala Thr
         50                  55                  60

Phe Lys Met Lys Lys Thr Val Asn Thr Val Trp Phe Val Asn Leu Ala
 65                  70                  75                  80

Val Ala Asp Phe Leu Phe Asn Ile Phe Leu Pro Met His Ile Thr Tyr
```

```
                         85                  90                  95
Ala Ala Met Asp Tyr His Trp Val Phe Gly Lys Ala Met Cys Lys Ile
            100                 105                 110

Ser Asn Phe Leu Leu Ser His Asn Met Tyr Thr Ser Val Phe Leu Leu
            115                 120                 125

Thr Val Ile Ser Phe Asp Arg Cys Ile Ser Val Leu Leu Pro Val Trp
            130                 135                 140

Ser Gln Asn His Arg Ser Ile Arg Leu Ala Tyr Met Thr Cys Ser Ala
145                 150                 155                 160

Val Trp Val Leu Ala Phe Phe Leu Ser Ser Pro Ser Leu Val Phe Arg
            165                 170                 175

Asp Thr Ala Asn Ile His Gly Lys Ile Thr Cys Phe Asn Asn Phe Ser
            180                 185                 190

Leu Ala Ala Pro Glu Ser Ser Pro His Pro Ala His Ser Gln Val Val
            195                 200                 205

Ser Thr Gly Tyr Ser Arg His Val Ala Val Thr Val Thr Arg Phe Leu
            210                 215                 220

Cys Gly Phe Leu Ile Pro Val Phe Ile Ile Thr Ala Cys Tyr Leu Thr
225                 230                 235                 240

Ile Val Phe Lys Leu Gln Arg Asn Arg Leu Ala Lys Asn Lys Lys Pro
            245                 250                 255

Phe Lys Ile Ile Ile Thr Ile Ile Thr Phe Phe Leu Cys Trp Cys
            260                 265                 270

Pro Tyr His Thr Leu Tyr Leu Leu Glu Leu His His Thr Ala Val Pro
            275                 280                 285

Ser Ser Val Phe Ser Leu Gly Leu Pro Leu Ala Thr Ala Val Ala Ile
            290                 295                 300

Ala Asn Ser Cys Met Asn Pro Ile Leu Tyr Val Phe Met Gly His Asp
305                 310                 315                 320

Phe Arg Lys Phe Lys Val Ala Leu Phe Ser Arg Leu Ala Asn Ala Leu
            325                 330                 335

Ser Glu Asp Thr Gly Pro Ser Ser Tyr Pro Ser His Arg Ser Phe Thr
            340                 345                 350

Lys Met Ser Ser Leu Asn Glu Lys Ala Ser Val Asn Glu Lys Glu Thr
            355                 360                 365

Ser Thr Leu
370
```

                       .*.*.*..****.*.**

METHODS FOR IDENTIFICATION AND USES OF ANTI-INFLAMMATORY RECEPTORS FOR EICOSAPENTAENOIC ACID ANALOGS

CROSS-REFERENCE TO RELATED APPLICATION(S)

This application is a continuation of International Application No. PCT/US2004/006766 filed Mar. 5, 2004, which claims priority to U.S. provisional application No. 60/452,244, filed Mar. 5, 2003, the contents of which are incorporated in their entirety by reference.

STATEMENT REGARDING RESEARCH & DEVELOPMENT

The work leading to this invention was supported in part by National Institutes of Health (NIH) grants GM38765, DK60583 and P01-DE13499. The U.S. Government therefore may have certain rights in the invention.

TECHNICAL FIELD

This invention relates to the identification and uses of receptors that mediate anti-inflammatory activity, particularly to anti-inflammatory activity mediated by eicosapentaenoic acid analogs, and to uses of such receptors to screen candidate substances for anti-inflammatory activity.

BACKGROUND OF THE INVENTION

Clinical assessment of dietary supplementation therapy with omega-3 polyunsaturated fatty acids (w-3 PUFA) indicate that they have a beneficial impact in certain human diseases (1). Their molecular mechanisms of action in reducing local inflammation has remained unclear. w-3 PUFAs are held to act via several possible mechanisms, such as preventing conversion of arachidonic acid to proinflammatory eicosanoids, or serving as an alternative substrate for 5-lipoxygenase to produce less potent 5-series leukotrienes (2). Of interest, fish leukocytes rich in w-3 PUFA generate eicosanoids from eicosapentaenoic acid (EPA; C20:5 w-3) that play signaling roles (3). However, the appropriate receptor site(s) has remained unidentified.

There is a need in the art for the identification of the receptor site(s) that interact with noel eicosanoids to help better understand the mode of action of such therapeutic agents.

SUMMARY OF THE INVENTION

The essential fatty acid eicosapentaenoic acid (EPA) present in fish oils displays beneficial effects in a range of human disorders associated with inflammation including cardiovascular disease. Resolvin E1, a recently identified oxygenated product of EPA, a resolving analog, was prepared by total synthesis and in nanomolar range proved to dramatically reduce dermal inflammation, peritonitis, splenic dendritic cell migration and interleukin-12 production. A receptor for resolvin analogs, for example Resolvin E1 (denoted Reso-R1), that signals to attenuate cytokine induced nuclear factor (NF)-kB activation was identified. The results demonstrate novel counter-regulatory mechanisms in inflammation via receptor-ligand activation and provide the first evidence that EPA is a precursor to potent endogenous anti-inflammatory and endogenous host protective signals.

In one aspect, the invention provides a method for screening a candidate substance for anti-inflammatory activity that includes contacting a cell that expresses the Reso E receptor with the candidate substance and detecting a biological activity mediated by the Reso E receptor. As used herein, a Reso E receptor (Reso ER) is a polypeptide sequence with a receptor activity, and which in various embodiments, has at least 50%, at least 60%, at least 70% or at least about 80% identity with the Reso ER sequences according to SEQ. ID NO: 1; SEQ. ID NO: 2; SEQ. ID NO: 3 of FIG. 11. Sequence identity as used herein, is determined by any scientifically accepted method of calculating sequence identity, exemplified for example, by the BLAST programs in one embodiment, or FASTA programs that take into consideration conservative amino acid substitutions and stretches of regional identity in another embodiment.

In another aspect, the invention provides a method of identifying a receptor that mediates an anti-inflammatory activity of a resolvin substance that includes introducing a nucleic acid configured to express a G-protein coupled receptor (GPCR) into a cell that does not endogenously express the GPCR, contacting the cell with a substance comprising a resolvin; and detecting that the cell has a reduced cytokine induced activation of a NF-kB transcription factor relative to a cell not contacted by the substance. As used herein, in one embodiment, a GPCR is a polypeptide sequence having at least 30%, or at least 40% or at least 50% or at least 60% or at least 70%, or at least about 80% identical to the Reso ER sequences defined above, which has at least 7 membrane spanning domains determinable by a Kyton-Doolittle hydropathy plot, and which has an biological activity coupled to a GTP binding activity of a G-protein. In another embodiment, a GPCR sequence has at least 60%, or at least 70%, or at least about 80% sequence identity within the second intracellular loop of the mouse, rat, or human, Reso ER, or human ALX sequences depicted in FIG. 12 according to SEQ. ID NO: 4; SEQ. ID NO: 5; SEQ. ID NO: 6; and SEQ. ID NO: 7 and has at least 60%, or at least 70%, or at least about 80% sequence identity in the seventh transmembrane domain of as depicted FIG. 12 according to SEQ. ID NO: 8; SEQ. ID NO: 8; SEQ. ID NO: 9; SEQ. ID NO. 10; and SEQ. ID NO: 11.

In another aspect, the invention provides a method for screening a candidate substance for anti-inflammatory activity that includes detecting that the candidate substance alters an activity mediated by a GPCR receptor.

In another aspect, the invention provides method for identifying a substance that interacts with a receptor that mediates an anti-inflammatory activity that includes interacting a candidate substance with a receptor that reduces cytokine induced (NF)-κB activation.

In yet another aspect, the invention provides an isolated nucleic acid operably configured to express a nucleic acid that encodes a sufficient amount of a resolvin receptor polypeptide to mediate a biological response of the polypeptide when introduced into a cell. As used herein, a "resolvin receptor" is a receptor that interacts with any derivative of EPA that elicits an anti-inflammatory response.

In still another aspect, the invention provides a method of identifying a receptor that mediates an anti-inflammatory activity that includes, providing a small interfering RNA (siRNA) against a nucleic acid that encodes a candidate receptor, expressing the siRNA in a cell that expresses the candidate receptor, subjecting the cell to a condition that induces pro-inflammatory response, and detecting whether expressing the siRNA in the cell increases the pro-inflammatory response relative to a cell subjected to the condition but not expressing the siRNA. In one example embodiment, the pro-inflammatory response is increased production of a cytokine that mediates the pro-inflammatory response. In a more particular embodiment, the cytokine is IL-12.

While multiple embodiments are disclosed, still other embodiments of the present invention will become apparent to those skilled in the art from the following detailed description, which shows and describes illustrative embodiments of the invention. As will be realized, the invention is capable of modifications in various obvious aspects, all without departing from the spirit and scope of the present invention. Accordingly, the drawings and detailed description are to be regarded as illustrative in nature and not restrictive.

BRIEF DESCRIPTION OF THE DRAWINGS

FIG. 11 illustrates a comparison of Reso ER sequences from mouse, rat and human sources.

FIG. 12 illustrates a comparison of GPCR sequences in the second intracellular loop and seventh transmembrane domain of mouse, rat and human Reso ER sequences and a human ALX sequence.

DETAILED DESCRIPTION OF PREFERRED EMBODIMENTS

In the detailed description that follows, citation is made to various references that may aid one of skill in the art to understand or practice the invention in its fullest scope. Each such reference is incorporated herein by reference, to the extent the teaching of those references do not conflict with the teachings provided herein.

Clinical assessment of dietary supplementation with omega-3 polyunsaturated fatty acids (w-3 PUFA) indicate their beneficial impact in certain human diseases particularly those in which inflammation is suspected as a key component in pathogenesis (1-3). Their molecular bases of action in reducing disease and local inflammation is important and of interest given the heightened awareness that inflammation and resolution is a major mechanisms in many diseases including cardiovascular disease, arthritis, Alzheimer's disease, asthma and periodontitis (4,5). w-3 PUFAs are widely held to act via several possible mechanisms, such as preventing conversion of arachidonate to proinflammatory eicosanoids, or serving as an alternative substrate producing less potent products (1). Of interest, fish leukocytes rich in w-3 generate mediators from eicosapentaenoic acid (EPA) that play signaling roles (6). However, the pathophysiological role of leukotriene and prostanoid-like compounds from EPA remains uncertain in humans as many of these molecules' role(s) are unknown.

Figure 1:
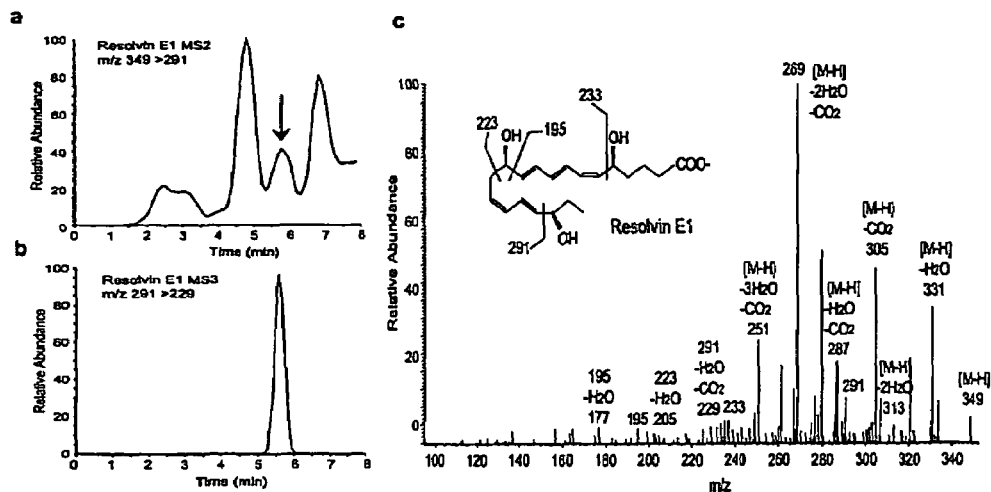
FIG. 1. Lipidomic analysis of Resolvin E1 in human blood. (a) Representative MS/MS selected ion chromatogram at m/z 291, (b) MS3 selected ion chromatogram at m/z 229 and (c) MS/MS (at m/z 349) spectrum of Resolvin E1 in human plasma.

Recently, the present inventors discovered a novel family of aspirin-triggered bioactive lipids biosynthesized during the spontaneous resolution phase of acute inflammation in vivo. This family of bioactive lipids have been termed the Resolvins (resolution-phase interaction products), are described in more detail in U.S. patent application Ser. No. 10/639,714, filed Aug. 12, 2003, entitled "Resolvins: Biotemplates for Novel Therapeutic Interventions" and in PCT application No. PCT/US03/25336, filed on Aug. 12, 2003 and entitled the same, which are incorporated herein by reference in their entirety. The Resolvins are potent autacoids, which now can provide molecular means that underlie w-3 PUFA's protective actions (7,8). At local sites, aspirin treatment enables EPA conversion to the novel 18R series of oxygenated products that carry potent counterregulatory signals. One of the main compounds of this 18R series, namely 5,12,18R-trihydroxyeicosapentaenoic acid (termed Resolvin E1) can arise via cell-cell interactions in murine inflammatory exudates, also exemplified with human vascular endothelium carrying aspirin-acetylated cyclooxygenase (COX)-2 and leukocytes possessing 5-lipoxygenase (LO) (7). Here, Resolvin E1 was generated in healthy human volunteers given EPA and aspirin, plasma values ranging 0.1 to 0.4 ng/ml for 6 donors using liquid chromatography-tandem mass spectrometry (LC-MS/MS) (FIG. 1). Formation is consistent with the scheme that endothelial cells expressing COX-2 treated with aspirin transform vascular EPA and release 18R-HEPE. When leukocyte and endothelial cell interact within the vasculature, 18R-HEPE is rapidly converted to Resolvin E1 via transcellular biosynthesis (FIG. 2a).

Figure 2:
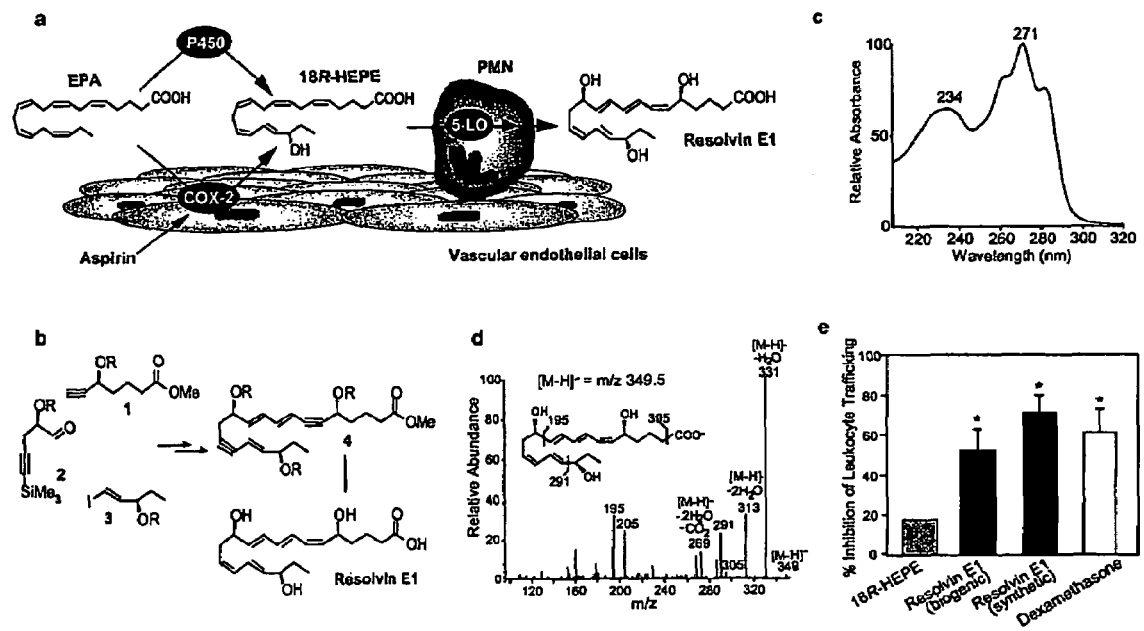
FIG. 2. (a) Resolvin E1 generation from EPA. Human endothelial cells expressing COX-2 treated with ASA transform EPA by abstracting hydrogen at C16 to give R insertion of molecular oxygen to yield 18R-H(p)EPE. Alternatively, cytochrome P450 monooxygenase can convert EPA to 18R-HEPE (25). They are further converted via sequential actions of leukocyte 5-LO and leads to formation of Resolvin E1. (b) Total organic synthesis of Resolvin E1. Precursors 1-3 were prepared in isomerically pure form from starting materials with known stereochemistry and coupled sequentially to form acetylenic intermediate 4, which was selectively hydrogenated to form isomerically pure Resolvin E1. (c) UV spectrum and (d) MS/MS spectrum of synthetic Resolvin E1. (e) Inhibition of leukocyte trafficking in murine dorsal air pouch. Values represent mean+SEM from 5 different mice, *P<0.05 (vs. vehicle control).

To assign the complete stereochemistry of the main 18R series Resolvin E1 and establish its biological activities, biogenic Resolvin E1 was prepared (7), and matched with synthetic Resolvin E1 (5S,12R,18R-trihydroxy-6Z,8E,10E, 14Z,16E-eicosapentaenoic acid) having complete stereochemistry that was prepared by total organic synthesis from isomerically pure precursors (FIG. 2b). A geometric isomer carrying all-trans conjugation at both carbon 6 and 14 positions in native Resolvin E1 was also prepared by organic synthesis to establish chromatographic properties as described in the supplementary examples of this description. Since Resolvin E1 is produced in subnanogram amounts in vivo, both synthetic and biogenic materials were prepared for matching their physical properties using UV spectroscopy, LC-MS/MS, GC-MS, and importantly to compare biological activities. The matching synthetic compound eluted beneath a single peak in HPLC with UV absorbance maximum 271 nm and 234 nm, indicative of conjugated triene and diene in the molecule (FIG. 2c). MS/MS fragmentation ions were essentially identical with the biogenic material namely a parent ion at m/z 349=[M-H]- and diagnostic product ions at m/z=291 and 195 (FIG. 2d). Results of physical matching studies are summarized in The Supplementary Examples.

Administration of as little as 100 ng/mouse of synthetic Resolvin E1 stopped leukocyte infiltration into inflammatory loci by 50-70% in TNF-a induced dorsal air pouch, which proved to be as potent as the biogenic material (FIG. 2e). For comparison in this model, local administration of dexamethasone (10 mg/mouse) gives 60% inhibition (FIG. 2e) and aspirin (1.0 mg/mouse) gives 70% inhibition of leukocyte recruitment (9), indicating that Resolvin E1 at 100 ng/mouse is orders of magnitude more potent than dexamethasone or aspirin in stopping leukocyte infiltration. Also indomethacin (100 ng/mouse) gave 25% inhibition and Resolvin E1 (100 ng/mouse) gave 50-60% inhibition of leukocyte recruitment in zymosan-induced peritonitis as described in The Supplementary Examples. The18S isomer gave essentially equivalent activity as native Resolvin E1 containing 18R, whereas the 6-trans,14-trans isomer showed reduced potency (~70%) for reducing leukocyte infiltration in zymosan-induced peritonitis. Based on matching of physical and biological properties, the 18R series Resolvin E1, a potent anti-inflammatory lipid mediator, was assigned the complete structure 5S,12R,18R-trihydroxy-6Z,8E,10E, 14Z,16E-eicosapentaenoic acid.

The murine airpouch is widely used to assess dermal inflammation and arthritis (FIG. 2e). The murine airpouch is characterized by a cavity and a lining composed of both fibroblast-like and macrophage-like cells (10). Intrapouch application of TNF-a evokes leukocyte infiltration by stimulating local release of chemokines and chemoattractants that are often produced by fibroblasts and phagocytes via regulation of nuclear factor (NF)-kB transcription factors (11). Systemic administration of Resolvin E1 dramatically attenuated leukocyte recruitment (FIG. 2e), meaning that receptor target for Resolvin E1 was expressed in those cells which counterregulates TNF-a induced NF-kB activation.

Figure 3:
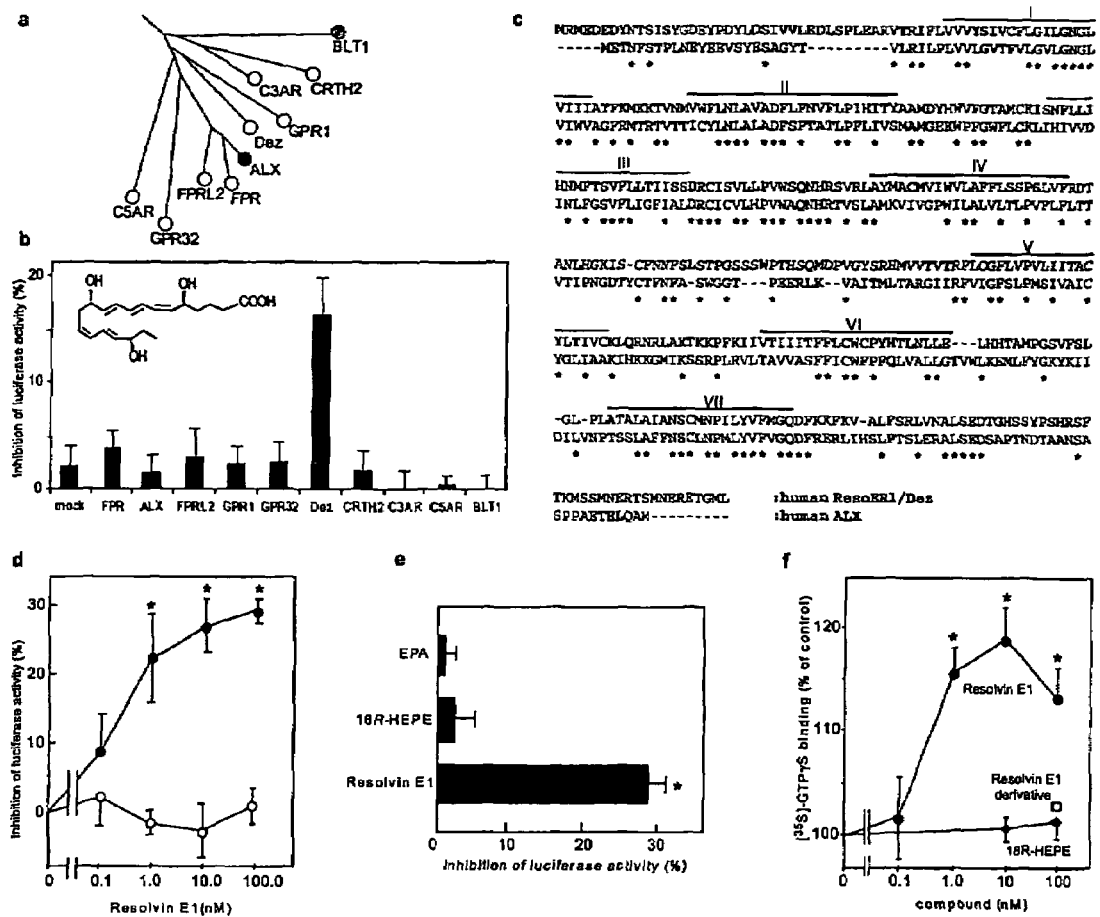
FIG. 3. (a) Phylogenetic tree representing amino acid sequence similarities between the human LXA4 receptor (ALX) and related GPCRs. (b) Functional screening for Resolvin E1 receptors. HEK293 cells co-transfected with pNF-kB-Luciferase and pcDNA3-GPCRs were exposed to Resolvin E1 (10 nM) and TNF-a. (c) Amino acid sequence alignment of human Reso ER1 with ALX. Asterisks indicate conserved amino acids. Putative transmembrane domains are lined and labeled as I-VII. (d) Resolvin E1 inhibits luciferase activity in a concentration dependent manner on cells transfected with pcDNA3-Reso ER1 (filled circle) but not pcDNA3 (open circle). (e) Ligand specificity for Reso ER1. Cells transfected with pcDNA3-Reso ER1 were exposed to 100 nM of each compound. Results are expressed as percent inhibition of luciferase activity and represent the mean+SEM from n=3 (b) or n=4 (d.e), *P<0.05. (f) Actions of Resolvin E1 (filled circle), Resolvin E1 derivative (6,14-diacetylenic-Resolvin E1, open rectangle) and 18R-HEPE (filled diamond) on [35S]-GTP-gS binding to membrane expressing Reso ER1. Results are expressed as a percentage of vehicle control with the mean+SEM (n=3). *P<0.05.

Resolvin E1 and Lipoxin (LX) A4 have different structures, are formed via different biosynthetic pathways and precursors (EPA vs arachidonate), yet they appear to share redundant beneficial properties that dampen excessive leukocyte recruitment (12), hence the present invention is based, at least in part, on recognizing that Resolvin E1 receptors share similar structural features to LO-derived eicosanoid receptors such as LXA4 receptor (ALX) and Leukotriene B4 receptor (BLT) (13). FIG. 3a shows a branch of the phylogenetic tree of human ALX with closely related G-protein coupled receptors (GPCRs). Expression plasmids of each GPCR were introduced into HEK293 cells and the ability of Resolvin E1 to inhibit TNF-a stimulated NF-kB activation was monitored by co-transfection with NF-kB response element-luciferase reporter plasmid. This permitted analysis of the activation of the relevant post ligand-receptor "stop" signaling for downregulation of NF-kB activation as for example demonstrated with ALX-transfected cells and its ligands (14). Among those screened (FIG. 3b), a putative orphan receptor denoted earlier as Dez/ChemR23 (15) was specifically activated by Resolvin E1 and at 10 nM inhibited NF-kB activation (FIG. 3b). In view of these results, the Dez receptor is herein termed "Reso ER1." Reso ER1 shares 36.4% identity with ALX in deduced amino acid sequences and of note contains a highly conserved domain within its second intracellular loop (75%) and seventh transmembrane region (69.5%) (FIG. 3c).

Resolvin E1 gave concentration dependent inhibition of TNF-a induced NF-kB activation with an EC50 of ~1.0 nM in Reso ER1 transfected cells but not in mock transfected cells (FIG. 3d). In this system, 1 mM aspirin, a known inhibitor of NF-kB at high concentrations namely millimolar range (16), gave non-receptor dependent inhibition of 26.2+ 4.9% for Reso ER1 transfected cells. Neither EPA nor 18R-HEPE at 100 nM, both metabolic precursors of Resolvin E1, inhibited NF-kB in Reso ER1 transfected cells (FIG. 3e). The isomer 6-trans,14-trans at 100 nM showed reduced potency for NF-kB inhibition that was essentially the same magnitude reduction in vivo. The functional interactions between Reso ER1 and G proteins using ligand-dependent binding of [35S]-GTPgS, a hydrolysis resistant GTP analog were also examined. Specific [35S]-GTPgS binding in isolated membranes obtained from cells expressing Reso ER1 increased selectively with Resolvin E1 in a concentration-dependent manner (FIG. 3f). These results indicate that Resolvin E1 transmits signal as a selective agonist via Reso ER1 and counterregulates TNF-a stimulated NF-kB activation.

Figure 4:
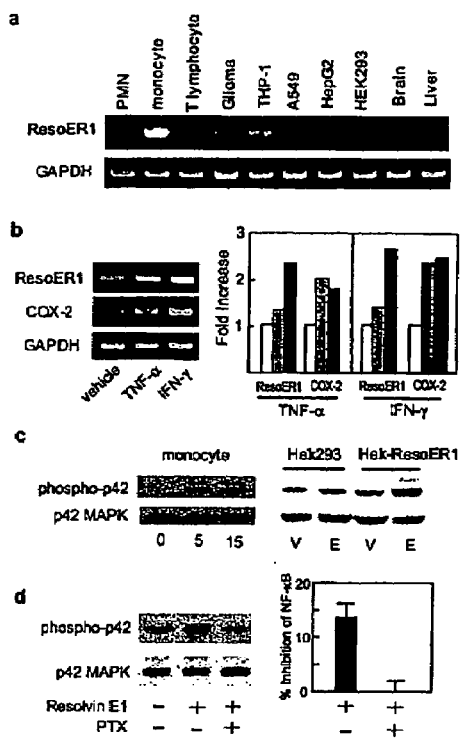
FIG. 4. (a) RT-PCR analysis of human peripheral blood leukocytes and glioma (DBTRG-05MG), monocytic (THP-1), lung epithelial (A549), hepatoma (HepG2), embryonic kidney (HEK293) cell lines, and brain and liver. (b) RT-PCR analysis of human peripheral blood monocytes exposed to either buffer alone, TNF-a (10 ng/ml), or IFN-g (25 ng/ml) for 6 h (gray) and 24 h (black). Expression levels were quantified by NIH image, normalized by GAPDH levels and expressed as fold increase over vehicle-treated cells. (c) MAP kinase activation in human peripheral blood monocytic cells and HEK-Reso ER1 cells treated with 100 nM Resolvin E1 (E) or vehicle (V). (d) Pertussis toxin (PTX) blocks Resolvin E1-induced ERK activation and NF-kB inhibition in HEK293 cells expressing Reso ER1.
Figure 8:
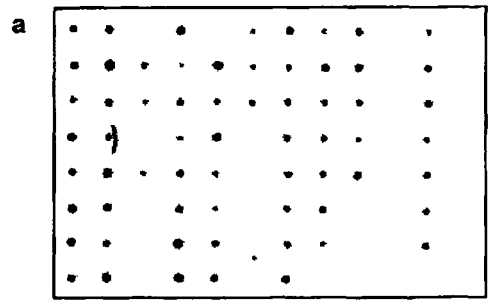
FIG. 8 illustrates expression pattern of Reso ER1 in various human tissues by dot blot hybridization.
Figure 9:
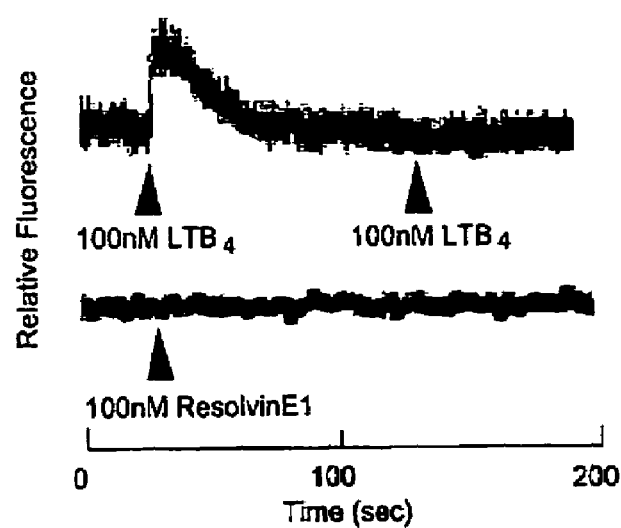
FIG. 9 illustrates calcium mobilization in human monocytes.
Figure 10:
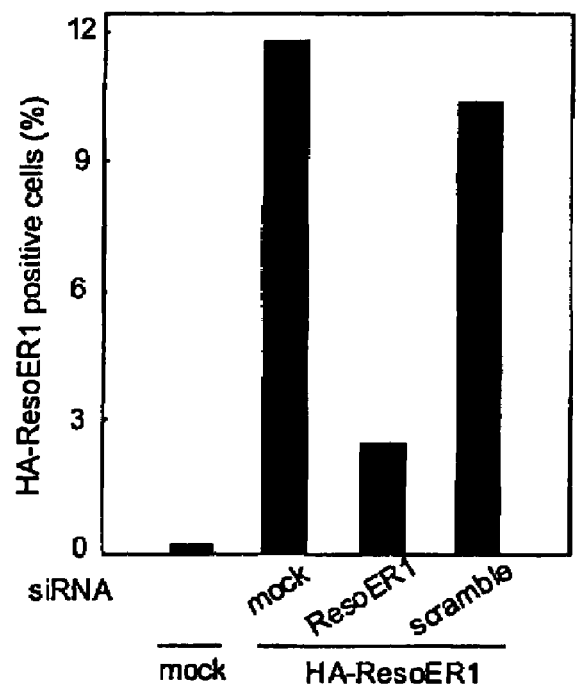
FIG. 10 illustrates siRNA-directed silencing of Reso ER1 expression in HEK293 cells.

Tissue distribution of human Reso ER1 was determined with dot blots containing mRNAs from human tissues that showed expression of Reso ER1 in several tissues such as cardiovascular system, brain, kidney, gastrointestinal tissues and myeloid tissues as is illustrated in FIG. 8. Also, a murine receptor counterpart was found in developing bone using in situ hybridization (17). Among the human peripheral blood leukocytes, Reso ER1 was abundantly expressed in monocytes, with lower amounts in neutrophils and T lymphocytes (FIG. 4a), findings consistent with the observation that this receptor is expressed in antigen-presenting cells (APC) such as macrophage and dendritic cells (15). Both monocyte Reso ER1 and COX-2 transcripts were highly upregulated by treatment with inflammatory cytokines such as TNF-a and IFN-g, and Reso ER1 showed delayed induction to that of COX-2 (FIG. 4b). Resolvin E1 increased phosphoryation of extracellular signal-regulated kinase (ERK) mitogen-activated protein (MAP) kinase both in peripheral blood monocytes and HEK293-Reso ER1 cells, but not in mock-transfected HEK293 cells (FIG. 4c). In addition, treatment of HEK293-Reso ER1 with pertussis toxin (PTX) abolished Resolvin E1 dependent ERK activation and NF-kB inhibition, indicating coupling to Gai/o-protein for the signal transduction (FIG. 4d). As shown in FIG. 9, Resolvin E1 did not evoke a calcium mobilization with either human peripheral blood monocytes or HEK-Reso ER1 stable transformants, and at 100 nM did not inhibit calcium mobilization by 100 nM LTB4 (data not shown). These results demonstrate that Resolvin E1 activates Reso ER1, evokes ERK phosphorylation and regulates gene expression, through Gi/o-protein.

Figure 5:
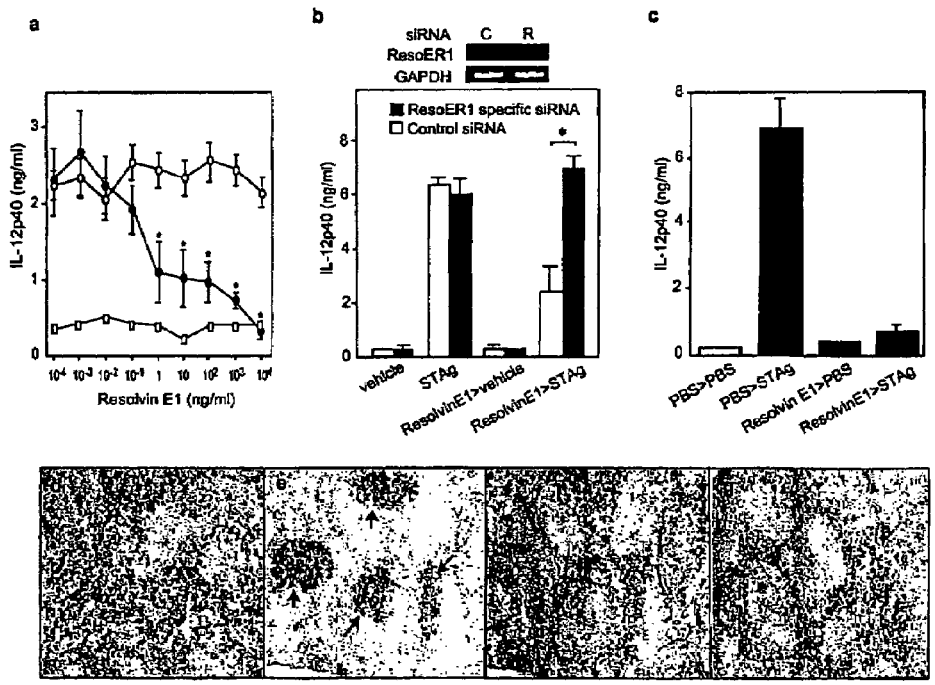
FIG. 5. (a) Resolvin E1 inhibits DC EL-12 production in vitro stimulated by pathogen extract (STAg) and expression of Reso ER1 specific siRNA enhances IL-12 production. CD11c+DCs incubated with vehicle (open circle) or Resolvin E1 (closed circle) before STAg or no STAg (open square). (b) Reduction of Reso ER1 expression by siRNA eliminates Resolvin E1 signaling. Expression of Reso ER1 and GAPDH mRNA were determined by RT-PCR from DCs treated with either control(C) or Reso ER1(R) specific siRNAs (inset). Spleen cell suspensions transfected with siRNAs were treated with vehicle (ethanol, 0.1% v/v) or Resolvin E1 (1.0 mg/ml). Eight hours later cells were stimulated with STAg (10 mg/ml) and IL-12p40 was measured. Bars represent mean±SD (n=3), *P<0.05 (control vs. specific siRNA). (c) Resolvin E1 blocks IL-12 production in vivo. Mice administered with either 100 ng Resolvin E1 or vehicle were challenged intraperitoneally with PBS or STAg, and IL-12p40 secretion from splenic CD11c+DCs was measured. (d-g) Resolvin E1 blocks trafficking of CD11c+DCs in spleen with pathogen extract challenge. Spleens from mice given 10 mg Resolvin E1 or vehicle were stained for CD11c. (d) PBS plus vehicle (e) STAg plus vehicle (f) PBS plus Resolvin E1 (g) STAg plus Resolvin E1. Arrows indicate CD11c positive DCs accumulated in T cell enriched area.

Given expression of human Reso ER1 in APCs, and since APC function is influenced by dietary w-3 PUFA supplementation (18), the activity of Resolvin E1 on APC function was examined using a microbial pathogen model. Injection of pathogen extract derived from *Toxoplasma gondii* (STAg) causes activation of splenic dendritic cells (DCs) to mobilize to T cell enriched areas where they produce high amounts of IL-12 (19). Addition of increasing concentrations of Resolvin E1 to isolated mouse splenic CD11c+DCs markedly inhibited IL-12p40 production by STAg within the nanomolar range (FIG. 5a).

siRNA experiments were carried out to reduce Reso ER1 in splenic DCs. The mouse ResoER receptor (17), which shares 80.3% identity with human Reso ER1, was also present in splenic DCs. Resolvin E1's action in regulating IL-12 production from DCs was eliminated by treatment with a siRNA specific for the mouse Reso ER1 (FIG. 5b). It was confirmed that this siRNA treatment dramatically reduced Reso ER1 mRNA expression in DCs (FIG. 5b, inset) and cell-surface expression of recombinant Reso ER1 in HEK293 cells as described in the Supplementary Example. These results confirm that Resolvin E1's anti-inflammatory action is mediated via Reso ER1. In vivo treatment with Resolvin E1 also blocked IL-12 production (FIG. 5c) as well as DC migration into T cell areas of the spleen (FIG. 5d-g).

Acute inflammation is a protective host response to foreign challenge or tissue injury that could lead to, if unopposed, loss of tissue structure as well as function. In many chronic disorders, prolonged and unresolved inflammation is believed to contribute to pathogenesis (4). Resolution of inflammation is an active process controlled by endogenous mediators that can counterregulate pro-inflammatory gene expression and cell trafficking, as well as stimulate inflammatory cell clearance (11,20). The observation that cytokines upregulated Reso ER1 as well as COX-2 in monocytes indicates that in scenarios where COX-2 is induced during inflammation, monocytes as well as endothelial cells treated with aspirin can also potentially convert w-3 EPA into Resolvin E1 in concert with PMN (7), that may serve an autocrine and/or paracrine message to terminate further NF-kB activation and cytokine production in a temporal and spatially regulated fashion. Resolvin E1 is generated in healthy volunteers taking EPA and aspirin (FIG. 1). These results are consistent with the notion that COX-2 is also constitutively expressed in healthy vasculature in vivo (21, 22). Also, the results presented here support the notion that aspirin, in addition to its well-appreciated action to inhibit prostanoid formation, can exert its beneficial actions, in part, via EPA catabolic synthesis of 18R series Resolvin E1 that in turn interacts with receptors such as Reso ER1 to dampen further proinflammatory processes. It is likely that in vivo, Resolvin E1 can also interact with additional receptors, in addition to Reso ER1. Indeed, Resolvin E1 can, at higher concentrations (~0.5 mM), interact with recombinant LTB4 receptor BLT1 (7) and could potentially antagonize BLT1 and BLT2 receptors (23) in vivo. Endogenous chemically redundant anti-inflammatory lipid autacoids act with high affinities (nM range) and stereoselectivity on structurally related receptors as does aspirin triggered lipoxin A4 generated from arachidonic acid (24) to enhance resolution by "stopping" PMN recruitment and IL-12 production from APC. Together, the present findings provide an endogenous agonist driven and hst-protective molecular mechanism that can underlie some of the beneficial actions of co-3 EPA observed in many clinical situations (1-3) as well as identify novel components in endogenous anti-inflammation/resolution, exemplified by Resolvin E1 and one of its receptors Reso ER1 that are of interest as new checkpoint regulators (20) in the pathogenesis of a wide range of human diseases.

SUPPLEMENTARY EXAMPLES AND METHODS

Studies reported here were performed using protocols approved by Harvard Medical Area Standing Committee on Animals and human subjects in accordance with the Brigham and Women's Human Research Committee.

LC-MS/MS Analysis of Resolvin E1

Human plasma samples were collected at 4 hours after oral administration of fish oil supplement (Fish Oil Concentrate, Walgreens) containing EPA (1 g) and DHA (0.7 g) followed by aspirin (160 mg) at 3 h in six healthy volunteers. Plasma samples were extracted by C18 solid phase extraction with d4-LTB4 (Cascade) as internal standard for LC-MS/MS analysis (7) using a Finnigan LCQ liquid chromatography ion trap tandem mass spectrometer equipped with a LUNA C18-2 (100×2 mm×5 mm) column and UV diode array detector using mobile phase (methanol:water:

acetate at 65:35:0.01) from 0 to 8 min, ramped to methanol 8 to 30 min, with a 0.2 ml/min flow rate.

Murine Dorsal Air-Pouch Model

Dorsal air pouches were raised on male FvB mice (6-8 wk) by injecting 3 ml of sterile air subcutaneously on days 0 and 3. On day 6, 100 ng/mouse of compounds were injected into tail vein. Inflammation in the air-pouch was induced by intrapouch injection of mouse recombinant TNF-a (100 ng/pouch), and pouch lavages were collected at 4 h and cells were enumerated.

Zymosan Induced Peritonitis

For peritonitis, 100 ng/mouse of Resolvin E1 or related structures was injected into tail vein and followed by 1 ml zymosan A (1 mg/ml) into-the peritoneum. Peritoneal lavages were collected at 2 h and cells were enumerated.

GPCR cDNAs and Phylogenetic Tree

GPCR cDNAs were cloned by RT-PCR using specific primers designed according to the GenBank™ database; human FPR(P21462), ALX(P25090), FPRL2(P25089), GPR1(A55733), GPR32(O75388), Dez(Q99788), CRTH2 (Q9Y5Y4), C3AR(Q16581), C5AR(P21730), BLT1 (Q15722). mouse Reso ER1 (U79525). The phylogenetic tree was constructed using the "All Program" at the Computational Biochemistry Server at ETHZ (http://cbrg.inf.ethz.ch/Server/AllAll.html).

NF-kB Reporter Gene Assay

HEK293 cells (1.0' 105 cells) were transiently transfected with 50 ng pNF-kB-luciferase (Stratagene), 500 ng of either pcDNA3 or pcDNA3-GPCRs and the internal standard pRL-TK (Promega) using Superfect transfection reagent (Qiagen). After 24 h, cells were exposed to the test compounds for 30 min, stimulated with recombinant human TNF-a (1.0 ng/ml, BD Pharmingen) for 5 h. Luciferase activity was measured by the Dual-Luciferase reporter assay system (Promega). Basal induction of luciferase activity by TNF-a was >150-fold in this system. Efficient expression of GPCRs to the cell surface was observed by immunostaining using HA-tagged GPCR constructs. For PTX treatment, HEK293 cells were treated with PTX (200 ng/ml) for 24 h before stimulation.

[35S]-GTPgS Binding Assay

HEK293 cells stably expressing human Reso ER1 were homogenized in ice-cold TED buffer (20 mM Tris-HCl pH7.5/1 mM EDTA/5 mM MgCl2/1 mM DTT). Membrane fraction (10 mg) was incubated in 400 ml of GTP-binding buffer (50 mM Hepes, pH7.5/100 mM NaCl/1 mM EDTA/5 mM MgCl2/1 mM DTT) containing 0.1 nM [35S]-GTPgS (>1000 Ci/mmol, Amersham) and 10 mM GDP for 30 min at 30° C. The bound and unbound [35S]-GTPgS was separated by rapid filtration through GF/C filters, and counted by liquid scintillation. Nonspecific binding was determined in the presence of 50 mM unlabeled GTPgS. Basal [35S]-GTPgS binding was 81.6+1.5 cpm/mg protein.

Dot Blot Hybridization and RT-PCR

Hybridization to MTE array (CLONTECH) was carried out using 1.1 kb.p. fragment encoding open reading frame of Reso ER1 following the manufacturer's protocol. Primers used in amplifications are 5'-ATGAGAATGGAGGAT-GAAGA-3' and 5'-TCAAAGCATGCCGGTCTCC-3' for human Reso ER1, 5'-ATGGAGTACGACGCTTA CAA-3' and 5'-TCAGAGGGTACTGGTCTCCTTCT-3' for mouse Reso ER1, 5'-GCTGACTATGGCTACAAAAGCTGG-3' and 5'-ATGCTCAGGGACTTGAGGAGG GTA-3' for COX-2, 5'-GACCACAGTCCATGACATCACT-3' and 5'-TCCACCACCC TGTTGCTGTAG-3' for glyceraldehyde-3-phosphate dehydrogenase (GAPDH). Amplified products were confirmed by direct sequencing.

MAP Kinase Activation

MAP kinase activation in monocytes and HEK293 cells after treatment with 100 nM of each compound was determined. After incubations, cells were lysed in cold lysis buffer (50 mM Tris-HCl, pH 8.0, 150 mM NaCl, 0.5 mM EDTA, 1.0% NP-40, 0.5% sodium deoxycolate, 10 mM NaF, 10 mM sodium pyrophosphate) containing protease inhibitor cocktail (Sigma). 40 mg of protein was separated on SDS-PAGE and immunoblot was performed using anti-phospho-p44/42 MAP kinase (Cell Signaling) and anti-ERK (Santa Cruz) antibodies. For PTX treatment, HEK-Reso ER1 cells were incubated with or without PTX (200 ng/ml) for 24 h at 37° C. and ERK activation was monitored by addition of Resolvin E1 (100 nM) for 5 min.

Activation of Spleen Dendritic Cells with Pathogen Extract (STAg)

Experiments were performed essentially as in (19). STAg was prepared from sonicated *T. gondii* (RH strain) tachzoytes. For isolated DC experiments, 70-85% CD11c positive DCs were isolated from spleen. CD11c+DC suspensions (1.0×106 cells/ml) were spread into 96-well plates and incubated for 24 h with Resolvin E1 before the addition of STAg (5 mg/ml). After overnight culture, supernatants were collected and EL-12p40 was measured with a sandwich ELISA. For in vivo treatments, C57BL/6 mice (n=3 per group) were injected intravenously with 100 ng Resolvin E1. After 18 h the animals were challenged intraperitoneally with PBS (0.2 ml/mouse), STAg (5 mg/ml) and sacrificed after an additional 6 h. CD11c+DCs were isolated from spleen and IL12-p40 secretion was measured at 24 h. For DC migration, Splenic frozen section from mice treated as above but given 10 mg of Resolvin E1 or vehicle were stained for CD11c and counterstained with hematoxylin.

RNA Interference

Chemically synthesized siRNA for mouse Reso ER1 (5'-AACACUGUGUGGUUUGUCAACdTdT-3') and Non-specific control IX siRNA (5'-AUUGUAUGCGAUCGCA-GACUU-3') were from Dharmacon Research. Spleen cells (1.0×106 cells/ml) were transfected using Chariot (Active Motif) following manufacturers' instructions. Briefly, siRNA was mixed with Chariot transfection reagent and incubated at room temperature for 30 minutes. Spleen cells were plated in serum-free RPMI medium, 200 ng siRNA/Chariot solution was added and incubated for 2 h at 37° C., followed by adding 10% FCS RPMI to the cultures. To assure effective inhibition of gene expression, cells were further incubated for 30 h at 37° C. before STAg stimulation.

LC-MS/MS Data

Figure 6:
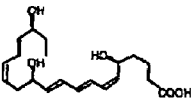
FIG. 6 is a table showing the structures of various molecules discussed in the present application along with LC-MS/MS data related thereto.
Figure 7:
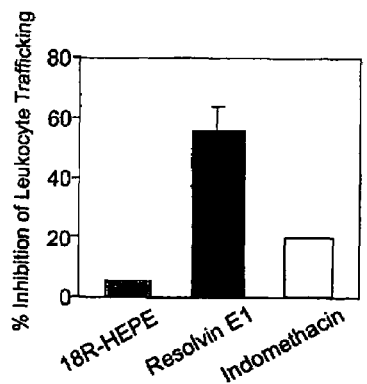
FIG. 7 illustrates inhibition of leukocyte infiltration in murine zymosan-induced peritonitis.

FIG. 6 illustrates results obtained from chromatographic analysis of synthetic and biogenic resolving E1.

For note (a) LC-MS/MS was performed with Finnigan LCQ liquid chromatography ion trap tandem mass spectrometer equipped with a LUNA C18-2 (100×2 mm×5 mm) column and a UV diode array detector using isocratic mobile phase (MeOH:H2O:AcOH at 65:35:0.01 (vol:vol:vol), with a 0.2 ml/min flow rate). For note (b) GC-MS was performed with a Hewlett-Packard 6890 equipped with a HP 5973 mass detector. A HP5MS cross-linked 5% ME siloxane column (30 m×0.25 mm×0.25 mm) was employed with a temperature program. The helium flow rate was 1.0 ml/min and the initial temperature was 150° C., followed by 230° C. (2 min), and 280° C. (10 min). Trimethylsilyl derivatives were prepared with each compound following treatment with diazomethane. For note (c) spectra were recorded in methanol.

Inhibition of Leukocyte Infiltration in Murine Zymosan-Induced Peritonitis.

18R-HEPE (100 ng), Resolvin E1 (100 ng), or Indomethacin (100 ng) was injected intravenously into mouse tails followed by zymosan A into the peritoneum. Mice were sacrificed, and peritoneal lavages were collected (2 h) and cells enumerated (n=3).

Effect of Pertussis Toxin (PTX) on Resolvin E1-Induced ERK Activation (a) and NF-kB Inhibition (b).

FIG. 4d illustrate effects of PTX on Resolvin E1 induced activation and NF-kB inhibition. In-(a) HEK-hReso ER1 cells were incubated with or without PTX (200 ng/ml) for 24 h at 37 C and ERK activation was monitored by addition of Resolvin E1 (100 nM) for 5 min. In (b) HEK293 cells were transiently transfected with pcDNA-hReso ER1, pNF-kB-luciferase and pRL-TK. After 24 h with or without PTX (200 ng/ml), cells were exposed to Resolvin E1 (50 nM) for 30 min, stimulated with TNF-a (1.0 ng/ml) for 5 h, and luciferase activity was measured.

siRNA-Directed Silencing of Reso ER1 Expression in Hek293 Cells.

Hek293 cells (5.0×105 cells) were transiently co-transfected with haemagglutinin(HA)-tagged mouse Reso ER1 expression plasmid (pHM6-mReso ER1, 0.5 mg) and siRNA (1.5 mg) using Superfect (Qiagen). After 48 h, cells were harvested and stained with anti-HA monoclonal antibody 3F10 and FITC-anti-rat IgG (Roche) and analyzed for cell-surface expression of HA-mReso ER1 by flow cytometry.

REFERENCES

1. De Caterina, R., Endres, S., Kristensen, S. D., Schmidt, E. B. eds. N-3 fatty acids and vascular disease. Bi&Gi Publishers, Verona (1993).

2. Marchioli, R. et al. Dietary supplementation with n-3 polyunsaturated fatty acids and vitamin E after myocardial infarction: results of the GISSI-Prevenzione trial. Lancet 354, 447-455 (1999).

3. Albert, C. M. et al. Blood levels of long-chain n-3 fatty acids and the risk of sudden death. N. Engl. J. Med. 346, 1113-1118 (2002).

4. Weiss, U. eds. Insight: Inflammation, Nature 420, 845 (2002).

5. Funk, C. D. Prostaglandins and leukotrienes: advances in eicosanoid biology. Science 294, 1871-1875 (2001).

6. Rowley, A. F., Hill, D. J., Ray, C. E., Munro, R. Haemostasis in fish, an evolutionary perspective. Thromb. Haemost. 77, 227-233 (1997).

7. Serhan, C. N. et al. Novel functional sets of lipid-derived mediators with antiinflammatory actions generated from omega-3 fatty acids via cyclooxygenase 2-nonsteroidal antiinflammatory drugs and transcellular processing. J. Exp. Med. 192, 1197-1204 (2000).

8. Serhan, C. N. et al. Resolvins: A family of bioactive products of omega-3 fatty acid transformation circuits initiated by aspirin treatment that counter proinflammation signals. J. Exp. Med. 196, 1025-1037 (2002).

9. Clish, C. B. et al. Local and systemic delivery of a stable aspirin-triggered lipoxin prevents neutrophil recruitment in vivo. Proc. Natl. Acad. Sci. USA 96, 8247-8252 (1999).

10. Lawrence, T., Willoughby, D. A., Gilroy, D. W. Anti-inflammatory lipid mediators and insights into the resolution of inflammation. Nature Reviews. 2, 787-795 (2002).

11. Tessier, P. A. et al. Chemokine networks in vivo. Involvement of C—X—C and C—C chemokines in neutrophil extravasation in vivo in response to TNF-a. J. Immunol. 159, 3595-3602 (1997).

12. McMahon, B., Mitchell, S., Brady, H. R., Godson, C. Lipoxins: revelations on resolution. Trends Pharmacol. Sci. 22, 391-395 (2001).

13. Yokomizo, T., Izumi, T., Chang, K., Takuwa, Y., Shimizu, T. A G-protein-coupled receptor for leukotriene B4 that mediates chemotaxis. Nature 387, 620-624 (1997).

14. Gewirts, A. T. et al. Lipoxin A4 analogs attenuate induction of intestinal epithelial proinflammatory gene expression and reduce the severity of dextran sodium sulfate-induced colitis. J. Immunol. 168, 5260-5267 (2002).

15. Samson, M. et al. ChemR23, a putative chemoattractant receptor, is expressed in monocyte-derived dendritic cells and macrophages and is a coreceptor for SIV and some primary HIV-1 strains. Eur. J. Immunol. 28, 1689-1700 (1998).

16. Kopp, E., Ghosh, S. Inhibition of NF-kB by sodium salicylate and aspirin. Science 265, 956-959 (1994).

17. Methner, A. et al. A novel G protein-coupled receptor with homology to neuropeptide and chemoattractant receptors expressed during bone development. Biochem. Biophys. Res. Commun. 233, 336-342 (1997).

18. Endres, S. The effect of dietary supplementation with n-3 polyunsaturated fatty acids on the synthesis of interleukin-1 and tumor necrosis factor by mononuclear cells. N. Engl. J. Med. 320, 265-271 (1989).

19. Aliberti, J., Hieny, S., reis e Sousa, C., Serhan, C. N., Sher, A. Lipoxin-mediated inhibition of IL-12 production by DCs: a mechanism for regulation of microbial immunity. Nature Immunol. 3, 76-82 (2002).

20. Nathan, C. Points of control in inflammation. Nature 420, 846-852 (2002).

21. Topper, J. N., Cai, J., Falb, D., Gimbrone, M. A., Jr. Identification of vascular endothelial genes differentially responsive to fluid mechanical stimuli: Cyclooxygenase-2, manganase superoxide dismutase, and endothelial cell nitric oxide synthase are selectively up-regulated by steady laminar shear stress. Proc. Natl. Acad. Sci. USA 93, 10417-10422 (1996).

22. Cheng, Y. et al. Role of prostacyclin in the cardiovascular response to thromboxane A2. Science 296, 539-541 (2002).

23. Yokomizo, T., Kato, K., Terawaki, K., Izumi, T., Shimizu, T. A second leukotriene B4 receptor, BLT2: A new therapeutic target in inflammation and immunological disorders. J. Exp. Med. 192, 421-431 (2000).

24. Serhan, C. N. Endogenous chemical mediators in anti-inflammation and pro-resolution. Curr. Med. Chem. 1, 177-192 (2002).

25. Capdevila, J. H. et al. The highly stereoselective oxidation of polyunsaturated fatty acids by cytochrome P450BM-3. J. Biol. Chem. 271, 22663-22671 (1996).

What is claimed is:

1. A method for screening a candidate substance for anti-inflammatory activity, comprising
   contacting a cell that expresses a Reso E receptor with the candidate substance; and
   detecting a biological activity mediated by the Reso E receptor, wherein the Reso E receptor is the murine Reso E receptor according to SEQ. ID NO: 2, a rat Reso E receptor according to SEQ. ID NO: 3 or human Reso ER1 according to SEQ. ID NO: 1, wherein the biological activity is reduced TNF-α cytokine induced activation of NF-kB transcription factor relative to a cell not contacted with the candidate substance.

2. The method of claim 1 wherein the cell is a leucocyte.

3. The method of claim 2 wherein the leucocyte is a monocyte, neutrophil, or a T-lymphocyte.

4. The method of claim 3 wherein the leukocyte is a monocyte that is an APC macrophage or dendritic cell.

5. The method of claim 1 wherein the Reso E receptor is human Reso ER1.

6. The method of claim 1 wherein the candidate substance comprises a resolvin molecule.

7. The method of claim 6 wherein the resolvin molecule is a poly-hydroxylated eicosapentaenoic acid (pH-EPA).

8. The method of claim 6 wherein the resolvin molecule is Reso-E1.

* * * * *